US011591628B2

(12) United States Patent
Douaisi et al.

(10) Patent No.: US 11,591,628 B2
(45) Date of Patent: Feb. 28, 2023

(54) BIOSYNTHETIC HEPARIN

(71) Applicant: Rensselaer Polytechnic Institute, Troy, NY (US)

(72) Inventors: Marc Douaisi, Troy, MI (US); Navdeep Grover, Troy, NY (US); Payel Datta, Troy, NY (US); Elena Paskaleva, Troy, NY (US); Lei Lin, Troy, NY (US); Paul Brodfuehrer, Troy, NY (US); Trevor J. Simmons, Troy, NY (US); Akihiro Onishi, Troy, NY (US); Makoto Hirakane, Troy, NY (US); Li Fu, Troy, NY (US); Kevin Li, Troy, NY (US); Robert J. Linhardt, Troy, NY (US); Jonathan Dordick, Troy, NY (US); Daisuke Mori, Troy, NY (US)

(73) Assignee: Rensselaer Polytechnic Institute, Troy, NY (US)

( * ) Notice: Subject to any disclaimer, the term of this patent is extended or adjusted under 35 U.S.C. 154(b) by 529 days.

(21) Appl. No.: 16/331,127

(22) PCT Filed: Sep. 7, 2017

(86) PCT No.: PCT/US2017/050385
§ 371 (c)(1),
(2) Date: Mar. 6, 2019

(87) PCT Pub. No.: WO2018/048973
PCT Pub. Date: Mar. 15, 2018

(65) Prior Publication Data
US 2019/0225998 A1 Jul. 25, 2019

Related U.S. Application Data

(60) Provisional application No. 62/384,341, filed on Sep. 7, 2016.

(51) Int. Cl.
| *C12P 19/26* | (2006.01) |
| *C08B 37/00* | (2006.01) |
| *C08B 37/08* | (2006.01) |
| *C12N 9/10* | (2006.01) |
| *C12P 19/04* | (2006.01) |
| *C08L 5/10* | (2006.01) |

(52) U.S. Cl.
CPC ............ *C12P 19/26* (2013.01); *C08B 37/003* (2013.01); *C08B 37/0069* (2013.01); *C08B 37/0075* (2013.01); *C08L 5/10* (2013.01); *C12N 9/10* (2013.01); *C12N 9/13* (2013.01); *C12P 19/04* (2013.01); *C12Y 208/02* (2013.01); *C12Y 208/02001* (2013.01)

(58) Field of Classification Search
CPC .... C12P 19/26; C08B 37/0075; A61K 31/727
See application file for complete search history.

(56) References Cited

U.S. PATENT DOCUMENTS

| 2009/0012278 A1* | 1/2009 | Takata | A61P 19/00 536/21 |
| 2009/0197308 A1 | 8/2009 | Liu et al. | |
| 2012/0270834 A1 | 10/2012 | Zhao et al. | |
| 2012/0322114 A1 | 12/2012 | Liu et al. | |
| 2014/0349962 A1* | 11/2014 | Rosenberg | C08B 37/0075 514/56 |

FOREIGN PATENT DOCUMENTS

| WO | WO-2012116048 A1 * | 8/2012 | ......... C08B 37/0078 |
| WO | WO-2014/204929 A2 | 12/2014 | |

OTHER PUBLICATIONS

Chen, J. et al. Enzymatic Redesigning of Biologically Active Heparan Sulfate, 2005, The Journal of Biological Chemistry, 280(52), 42817-42825 (Year: 2005).*
Vaidyanathan, D. et al "Engineered heparins as new anticoagulants" Bioeng. Trans. Med., vol. 2, pp. 17-30. (Year: 2017).*
Mulloy, B. et al "USP compendial methods for analysis of heparin . . . " Anal. Bioanal. Chem. vol. 406, pp. 4815-4823. (Year: 2014).*
Xiong, J. et al "Immobilized enzymes to convert N-sulfo, N-acetyl heparosan . . . " J. Biotechnol., vol. 167, pp. 241-247. (Year: 2013).*
Fu, L. et al "Structural characterization of pharmaceutical heparins . . . " J. Pharm. Sci., vol. 102, No. 5, pp. 1447-1457. (Year: 2013).*
Desai et al., "Measurement of the Antithrombin III Binding Sites in Low Molecular Weight Heparins by 13C NMR and Capillary Electrophoresis," Pharmaceutical Sciences, 1995, 1:349-353.
Laurent et al., "The Molecular-Weight-Dependence of the Anti-Coagulant Activity of Heparin," Biochem. J., Nov. 1, 1978, 175:691-701.
Office action in EP 17849497.7 dated Mar. 2, 2021.
Bhaskar et al., "Combinatorial one-pot chemoenzymatic synthesis of heparin," Carbohydrate Polymers, 2015 (online Nov. 7, 2014), 122:399-407.
Chen et al., "Enzymatic Redesigning of Biologically Active Heparin Sulfate," The Journal of Biological Chemistry, Dec. 30, 2005, 280(52):42817-42825.
Supplementary European Search Report dated Apr. 28, 2020, in EP 17849497.7.
International Search Report and Written Opinion of PCT/US2017/050385 dated Dec. 14, 2017.
Zhang et al., "Solution Structures of Chemoenzymatically Synthesized Heparin and its Precursors," Journal of the American Chemical Society, Sep. 4, 2008, 130(39):12998-13007.
Search Report and Written Opinion in SG 10202101954T dated May 6, 2022.
Wang et al., "Control of the heparosan N-deacetylation leads to an improved bioengineered heparin," Appl. Microbiol. Biotechnol., Jul. 2011,91(1):91-99.

* cited by examiner

*Primary Examiner* — Leigh C Maier
(74) *Attorney, Agent, or Firm* — Foley & Lardner LLP

(57) ABSTRACT

The present disclosure relates to synthesis of heparin, which may be bioequivalent to porcine USP Heparin Sodium. The synthesis may involve three intermediates starting from heparosan.

18 Claims, 4 Drawing Sheets

BIOSYNTHETIC HEPARIN

RELATED APPLICATIONS

The present application is a National Phase of International Patent Application No. PCT/US2017/050385 filed Sep. 7, 2017, which claims priority to U.S. provisional application No. 62/384,341 filed Sep. 7, 2016, which are both incorporated herein by reference in their entirety.

FIELD

The present disclosure relates in general to a field of polysaccharide chemistry and more particularly, to biosynthetic heparin, which may be bioequivalent to porcine USP Heparin; methods of making the biosynthetic heparin; intermediates, which may be used in the methods of making; and methods of using the biosynthetic heparin.

SUMMARY

One embodiment is a glycosaminoglycan comprising an amount of N-sulfated (NS) disaccharide group, which amount is effective to produce a biosynthetic heparin. The amount of the NS group disaccharide group may be 78-99% or 81-97% or 83-95% or 85-93%.

Another embodiment is a glycosaminoglycan comprising an amount of N-sulfated, 2-sulfated (NS2S) disaccharide group, which amount is effective to produce a biosynthetic heparin. The amount of the NS2S disaccharide group may be 44-80% or 50-78% or 55-77% or 60-76%.

Yet another embodiment is a glycosaminoglycan comprising amounts of N-sulfated, 2-sulfated, 6-sulfated (NS2S6S) disaccharide group and N-sulfated, 6-sulfated (NS6S) disaccharide group, wherein the amounts are effective to produce a biosynthetic heparin. Respective amounts of the NS6S group and the NS2S6S disaccharide groups may be 6-40% NS6S group and 31-73% NS2S6S group; 6-32% NS6S group and 36-70% NS2S6S group; 6-26% NS6S group and 40-67% NS2S6S group; or 6-22% NS6S group and 43-64% NS2S6S group.

Yet another embodiment is a method for producing a biosynthetic heparin, comprising: a. obtaining a glycosaminoglycan comprising 31-73% of NS2S6S disaccharide group, 6-40% of NS6S disaccharide group, 0-27% of NS2S group and 1-22% of NS group; and b. treating the glycosaminoglycan with an enzyme, which is 3-O-sulfotransferase isoform 1 (3OST-1), in the presence of a sulfate donor to produce a biosynthetic heparin batch.

Yet another embodiment is a method of making a second glycosaminoglycan intermediate comprising 44-80% of NS2S group and 13-39% of NS group. The method may comprise a. converting an amount of N-acetyl glucosamine residues in heparosan to produce a first glycosaminoglycan comprising 78-99% of N-sulfated (NS) disaccharide group, wherein the amount of the converted N-acetyl glucosamine residues corresponds to the amount of the NS group in the first glycosaminoglycan intermediate; and b. treating the first glycosaminoglycan intermediate with two enzymes, which are C5-epimerase (C5-epi) and 2-O-sulfotransferase (2OST), in the presence of a sulfate donor to produce the second glycosaminoglycan intermediate.

And yet another embodiment is a method of making a third glycosaminoglycan intermediate comprising 31-73% of NS2S6S disaccharide group, 6-40% of NS6S disaccharide group, 0-27% of NS2S group and 1-22% of NS group. The method may comprise treating a second glycosaminoglycan intermediate comprising 44-80% of NS2S group and 13-39% of NS group with an enzyme, which is 6-O-sulfotransferase isoforms 1 and/or 3 (6OST-1/3), in the presence of a sulfate donor to convert the second glycosaminoglycan intermediate to the third glycosaminoglycan intermediate.

FIGURES

FIG. 1 schematically shows the pathway from heparosan to biosynthetic heparin (BSH), which may be bioequivalent to porcine USP Heparin.

FIG. 2 schematically illustrates methods for analysis of intermediates and biosynthetic heparin, which may be bioequivalent to porcine USP Heparin.

DETAILED DESCRIPTION

Figure 1:
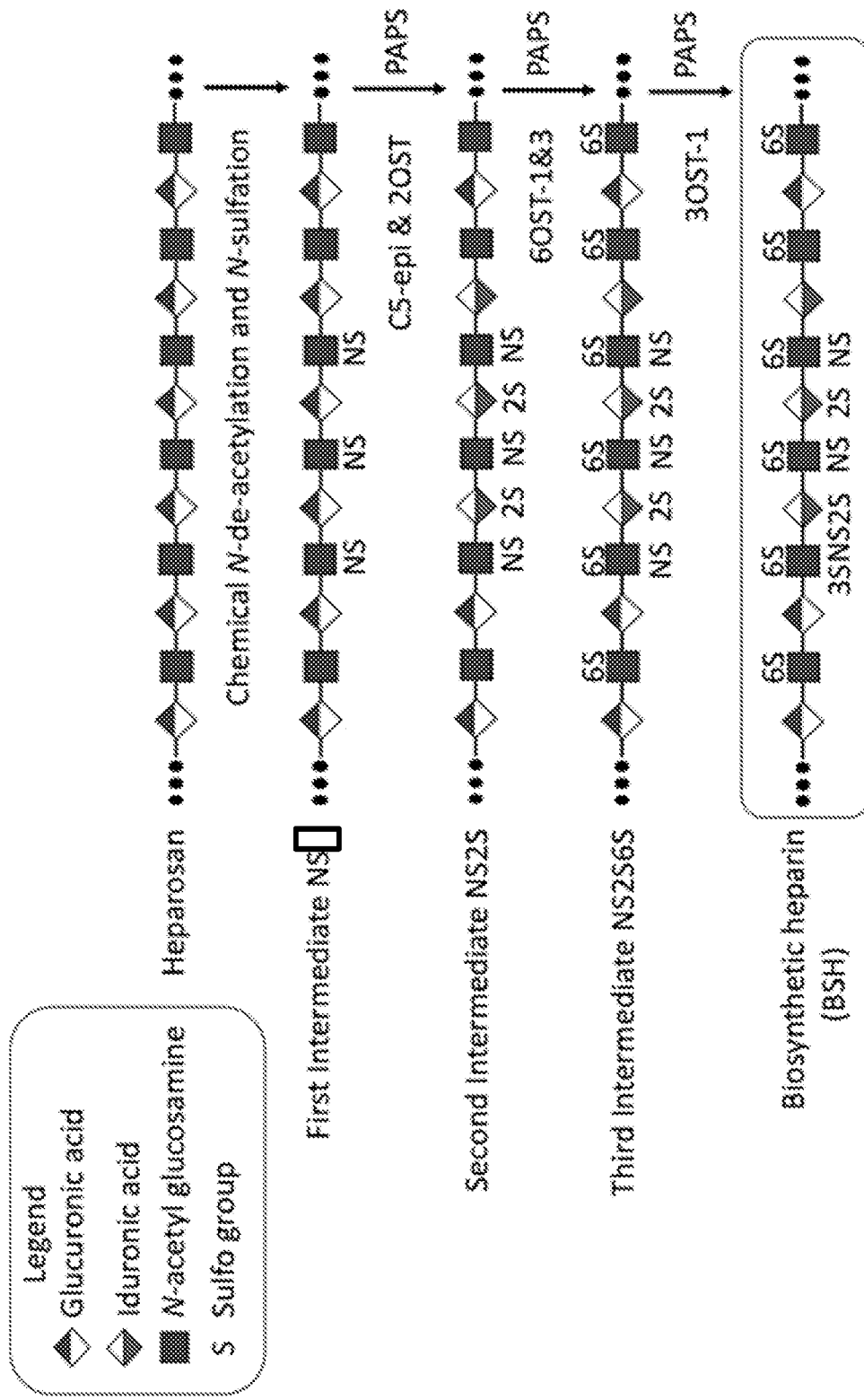
Figure 2:
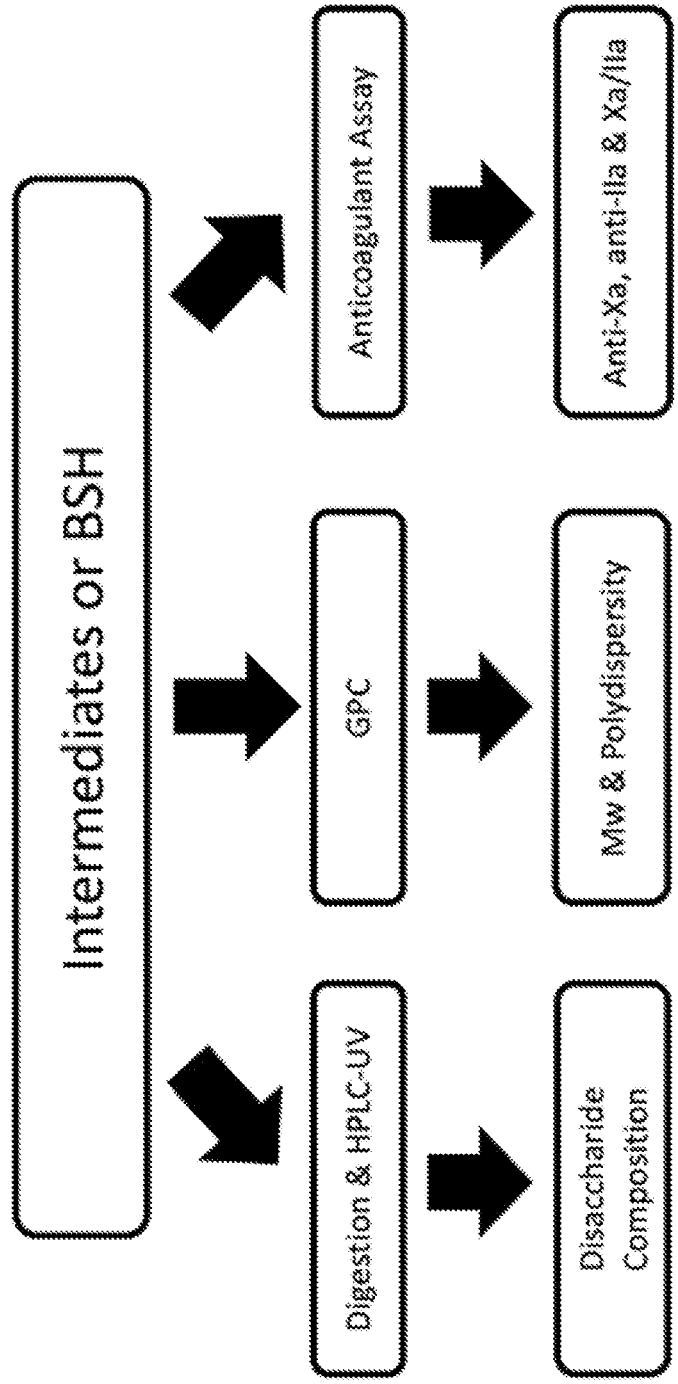

Heparin is widely used as an anticoagulant, both in solution and on implanted devices. Chemical synthesis of heparin is generally considered infeasible, and so pharmaceutical grade heparin has been derived from a variety of animal tissues throughout heparin production history. But the reliance on animal sources raises problems for quality control and supply.

The main source of heparin is porcine intestine, but bovine lung and intestinal heparin, and ovine intestinal heparin are also available. Product quality can vary with environmental factors and animal subspecies, providing additional difficulties for drug regulation. Serious concerns over prion diseases such as bovine spongiform encephalopathy (BSE, "mad cow disease"), which causes Creutzfeldt-Jakob disease in humans, and the scrapie prion in sheep have led to a decline in the use of bovine and ovine tissues as a source of heparin.

In 2008, an oversulfated chondroitin sulfate (OSCS) was introduced into heparin produced from pigs in China, leading to the death of nearly 100 Americans and a markedly reduced supply of heparin. This deliberate adulteration was very difficult to detect since the tissue supply chain for heparin in slaughterhouses lacks current good manufacturing practices (cGMP) oversight.

More recently, the mixing of heparin obtained from different animal species has been suspected. Bovine lung heparin, bovine intestinal heparin, ovine intestinal heparin and porcine intestinal heparin can be distinguished from one another by their different distribution of structural variants of the antithrombin pentasaccharide binding site as well as differences in their disaccharide compositions. However, it is very difficult to detect the presence of small amounts of bovine intestinal heparin or ovine intestinal heparin in a porcine intestinal heparin product even using current state-of-the-art analytical methods.

Supply is also a serious issue. Despite the 1.2 billion or more pigs that are slaughtered each year worldwide, leading to 100 tons/year of heparin, commercial suppliers may not be able to keep pace with increased worldwide demand, particularly in developing countries. Recent market share analysis showed that the majority of crude heparin is sourced from China, which supplies about 57% of the worldwide market. The susceptibility of animal populations to infectious disease, such as porcine epidemics in China, overharvesting, or environmental concerns can dramatically reduce the supply of animals from which heparin can be prepared. Spot shortages of heparin have led to serious consideration about the re-introduction of bovine heparin on the US market. However, bovine intestinal heparin fails to meet USP heparin specifications, and this limits its commercial use. Acceptance of bovine intestinal heparin also increases the risk of mixing porcine and bovine heparins, which is difficult to detect and alters properties of the final product.

In view of the need for alternative and reliable sources of bioequivalent heparin, researchers have attempted to synthesize heparin from heparosan. A combination of chemical and enzymatic steps gave a product that approached heparin but, to the best of the inventors' knowledge, biosynthetic heparin synthesized chemoenzymatically has yet to meet the USP standard. After diligent investigation in multiple test examples, the present inventors have synthesized heparin, which may meet all requirements of the USP. The inventors have elucidated three intermediates with specific features that may be necessary to obtain such bioequivalent heparin.

Definitions

For the purposes of the present application, the following terms have these definitions:

As used herein "a" or "an" means one or more, unless specifically indicated to mean only one.

"About" expressly encompasses the typical variation understood by the skilled person to be equivalent to a stated value. Where a numerical value is used, "about" encompasses±20% or ±15% or ±10% or ±8% or ±7% or ±6% or ±5% or ±3% or ±2% or ±1% of the stated value.

Where a % is provided regarding disaccharide content, it typically refers to the mol/mol percentage, unless otherwise stated.

As used herein BSH refers to biosynthetic heparin, i.e. heparin made through one or more of a chemical process; an enzymatic process; a combined chemical and enzymatic process; microbial and mammalian cell culture process. In some embodiments, the biosynthetic heparin may comprise heparin that is bioequivalent to porcine USP Heparin, i.e. porcine Heparin Sodium, e.g., "bioequivalent heparin".

As used herein "bioequivalent heparin" (BEqH) is equivalent to the porcine USP Heparin Sodium in terms of levels of activity and molecular weight distribution. In some embodiments, bioequivalent heparin may contain disaccharide groups NS, NS2S, NS6S and NS6S2S in amounts equivalent to porcine USP Heparin as disclosed in Table 2 below.

As used herein, the term "batch" may refer to a specific quantity of a drug or other material, such as heparin, that is intended to have uniform character and quality, within specified limits, and is produced according to a single manufacturing order during the same cycle of manufacture.

Heparin and Heparosan

Heparosan is a group of heterogeneous length straight-chain polysaccharides with the repeating disaccharide unit [→4) β-D-glucuronic acid (GlcA) (1→4) N-acetyl-α-D-glucosamine (GlcNAc) (1→]$_n$.

Heparin is a heterogeneous group of straight-chain anionic glycosaminoglycans having anticoagulant properties. Heparin may be digested into distinctive disaccharide groups (Yang, B., Chang, Y., Weyers, A. M., Sterner, E., & Linhardt, R. J. (2012). and analysis performed by liquid chromatography-ultraviolet spectrometry (LC-UV) method. (P. Mourier et al. Analytical Chemistry Research 3 (2015) 46-53). The data obtained from LC-UV method is highly comparable with conventionally used liquid chromatography-mass spectrometry (LC-MS) method. After digestion with a mixture of three heparin lyases, heparin affords the following disaccharides:

OS [ΔUA-GlcNAc]

NS: [ΔUA-GlcNS]

6S [ΔUA-GlcNAc6S]

2S [ΔUA2S-GlcNAc]

NS2S [ΔUA2S-GlcNS]

NS6S [ΔUA-GlcNS6S]

2S6S [ΔUA2S-GlcNAc6S]

TriS (NS2S6S) [ΔUA2S-GlcNS6S]

Where ΔUA corresponds to 4-deoxy-α-L-threo-hex-4-enopyranosyl uronic acid. GlcN corresponds to D-glucosamine, Ac corresponds to acetyl and S corresponds to sulfo. In this specification, the content of a disaccharide may be calculated based on the total content of the above eight disaccharides.

Because heparin and heparosan and related derivatives are complex molecules, they may also be characterized according to their weight average molecular weight (Mw) and molecular weight distribution. Heparin may further be characterized by its anticoagulant activity.

The United States Pharmacopeia version 39 (USP39) standard, "Heparin Sodium, USP" requires heparin to have specific levels of activity and molecular weight distributions. According to the USP, heparin has a weight average of 15,000-19,000 Da; the percentage of heparin chains with a molecular weight of greater than 24,000 Da are not more than 20% of the total; and the ratio of chains between molecular weights of 8,000 to 16,000 Da to chains between molecular weights of 16,000 to 24,000 Da is not less than 1.0.

In the present invention, the ratio of chains between molecular weights of 8,000 to 16,000 Da to chains between molecular weights of 16,000 to 24,000 Da is not less than 1.0, preferably between 1.0 and 2.5, 1.0 to 2.0, 1.2 to 1.8, 1.4-1.7, 1.5, or 1.6. Potency is determined by a biological assay using a USP reference standard based on units of heparin activity per milligram. These specifications require anticoagulant activity of heparin on factor IIa (i.e. anti-IIa) of not less than 180 U/mg, and the ratio of activity on factor Xa to factor IIa (i.e. anti-Xa/anti-IIa) is between 0.9 and 1.1.

The current USP monograph (USP 39) for porcine Heparin Sodium has no requirements related to disaccharide composition. However, it stands to reason that the properties of heparin follow from the structure. Therefore, the present inventors elucidated certain structural features of porcine USP Heparin. Table 1 shows the statistical range of disaccharide groups derived from porcine USP Heparin following treatment with three heparin lyases. A total of 15 lots of porcine USP Heparin were measured. Arithmetic mean (Mean) and standard deviation (SD) of the samples were calculated. Standard deviation of analytical error was obtained based on the present inventor's accumulated data. The following equation in the left most column of Table 1 was applied to calculate the range of each disaccharide.

TABLE 1

Compositional analysis of porcine USP-Heparin batches and determination of a target range for a biosynthetic heparin, which may be bioequivalent for porcine USP Heparin.

| (mol %) | | 0S | NS | 6S | 2S | NS6S | NS2S | 2S6S | TriS |
|---|---|---|---|---|---|---|---|---|---|
| Mean of 15 lots USP heparin | (=A) | 3.8 | 3.1 | 3.2 | 1.7 | 10.7 | 7.3 | 1.3 | 68.9 |
| SD of 15 lots USP heparin | (=B) | 0.99 | 0.55 | 0.32 | 0.15 | 0.92 | 0.61 | 2.0 | 1.4 |
| SD of overall analytical error (N = 12) | (=C) | 0.33 | 0.13 | 0.10 | 0.10 | 0.26 | 0.28 | 0.15 | 1.0 |
| BEqH target range Minimum (3sd) | (=A − 3*(B + C)) | 0.0 | 1.1 | 2.0 | 0.9 | 7.1 | 4.6 | 0.4 | 59.8 |
| BEqH target range Maximum (3sd) | (=A + 3*(B + C)) | 7.8 | 5.1 | 4.5 | 2.4 | 14.2 | 9.9 | 2.2 | 78.0 |
| BEqH target range Minimum (2sd) | (=A − 2*(B + C)) | 1.2 | 1.7 | 2.4 | 1.2 | 8.3 | 5.5 | 0.7 | 62.8 |
| BEqH target range Maximum (2sd) | (=A + 2*(B + C)) | 6.5 | 4.5 | 4.1 | 2.2 | 13.0 | 9.0 | 1.9 | 75.0 |
| BEqH target range Minimum (1sd) | (=A − *(B + C)) | 2.5 | 2.4 | 2.8 | 1.4 | 9.5 | 6.4 | 1.0 | 65.9 |
| BEqH target range Maximum (1sd) | (=A + *(B + C)) | 5.2 | 3.8 | 3.7 | 1.9 | 11.8 | 8.1 | 1.6 | 72.0 |

Assuming that the 15 samples of heparin are representative, 3 standard deviations encompasses 99.7% of the expected variation.

In some embodiments, the content of each disaccharide in the biosynthetic heparin, which is bioequivalent to the porcine USP Heparin Sodium, is within 3 standard deviations of the estimated mean derived from USP heparin, as shown in Table 1 above and provided in Table 2.

TABLE 2

Composition of porcine USP-heparins within the 3 standard deviation variability.

| mol % | 0S | NS | 6S | 2S | NS6S | NS2S | 2S6S | TriS |
|---|---|---|---|---|---|---|---|---|
| USP Heparin | 0-7.8 | 1.1-5.1 | 2.0-4.5 | 0.9-2.4 | 7.1-14.2 | 4.6-9.9 | 0.4-2.2 | 59.8-78.0 |

In some embodiments, the content of each disaccharide in the biosynthetic heparin is within 2.5, 2.0, 1.5 or 1.0 standard deviations of the estimated mean derived from USP heparin. In some embodiment embodiments, the content each of the major disaccharides, NS, NS6S, NS2S, and TriS, are within 3.0, 2.5, 2.0, 1.5 or 1.0 standard deviations of the respective estimated mean derived from USP heparin.

Figure 3:
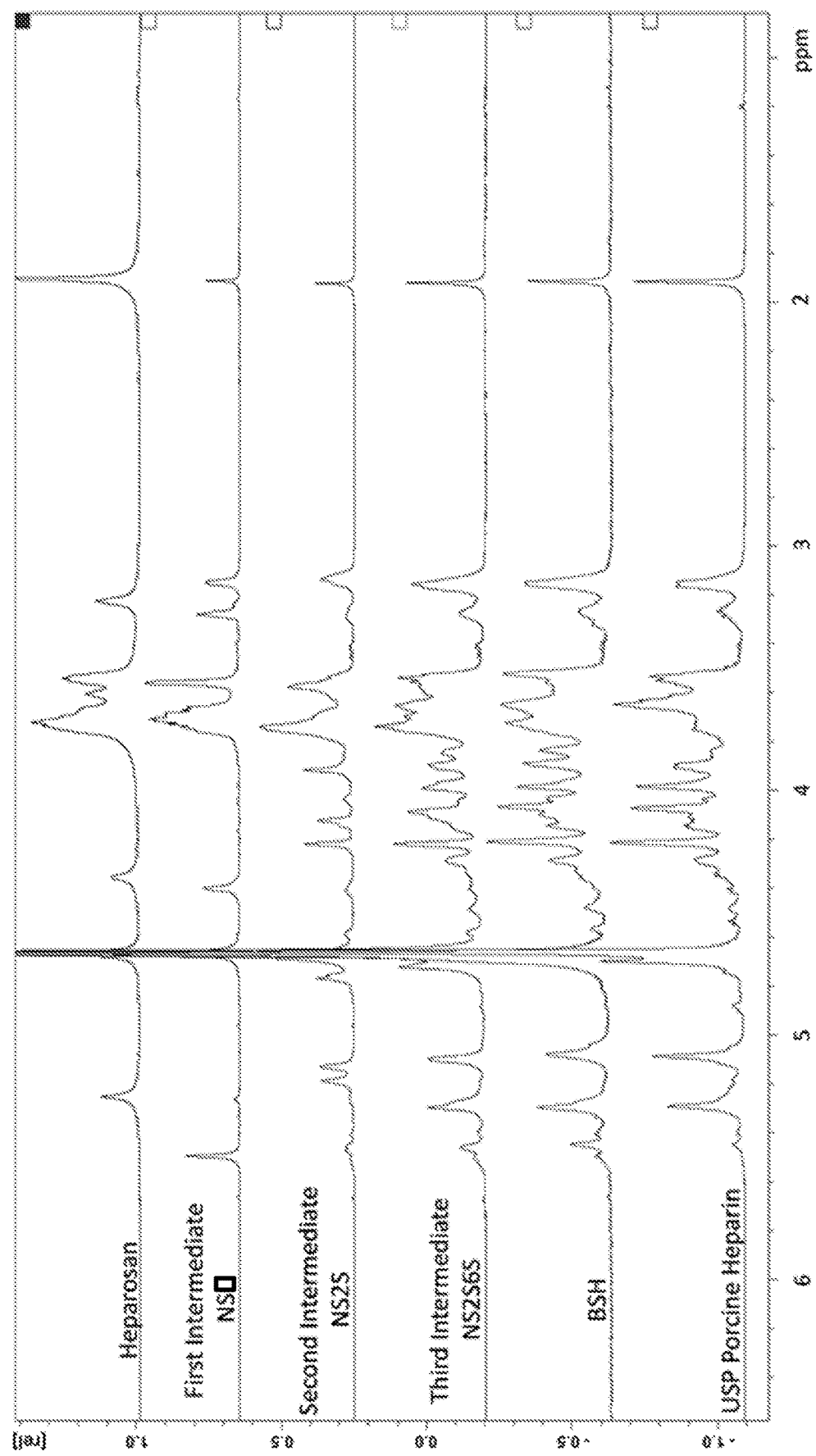
FIG. 3 shows 1D $^1$H-NMR spectra for heparosan, NS, NS2S, NS6S, NS2S6S intermediates, biosynthetic heparin, which may be bioequivalent to porcine USP Heparin, and porcine USP heparin.
Figure 4:
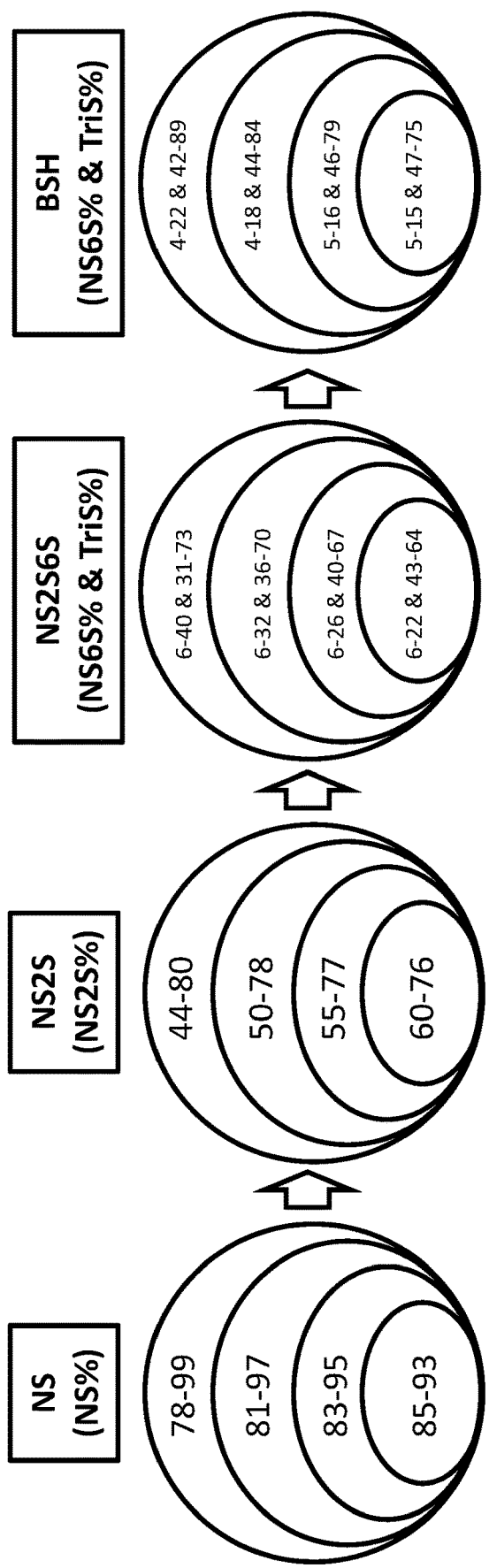
FIG. 4 shows exemplary compositional ranges of biosynthetic heparin intermediate structures, which may provide properties equivalent to porcine USP Heparin.

Mulloy et al. "USP compendial methods for analysis of heparin: chromatographic determination of molecular weight distributions for heparin sodium" *Anal Bioanal Chem* (2014) 406:4815-4823, reviewed size distributions of porcine USP heparin sodium. According to FIG. 3, the 8-16 kDa species were at most 55%, and the 16-24 kDa species were no less than 25%. Therefore, the 18-16/16-24 ratio was 2.2 (i.e. 55/25) in this study.

SYNTHESIS OF HEPARIN FROM HEPAROSAN

Heparosan is a polysaccharide with the repeating disaccharide unit [→4) β-D-glucuronic acid (GlcA) (1→4)N-acetyl-α-D-glucosamine (GlcNAc) (1→]$_n$. Heparosan is biosynthesized as a polysaccharide capsule in bacteria including *Escherichia coli* and *Pasteurella multicida*. Lindahl U et al. (1998) "Regulated diversity of heparan sulfate" *J. Biol Chem* 273(39):24979-24982. Laboratory-scale studies have shown that heparosan with a weight average molecular weight ($M_w$)>10,000, obtained from *E. coli* K5 strain can be chemoenzymatically converted to an anticoagulant polysaccharide called neoheparin, which is not bioequivalent to porcine USP heparin sodium. Lindahl et al. (2005) *J Med Chem* 48(2):349-352; Zhang et al. (2008) *Journal of the American Chemical Society* 130(39):12998-13007; U.S. Pat. No. 6,162,797; US 2014/0349962.

The following references describe biosynthetic heparins, which are not bioequivalent to porcine USP heparin sodium. None describe the production of the intermediates having the properties described herein, nor is the heparin produced bioequivalent to porcine USP Heparin. Where reported, the disaccharide content of such heparins is not within 1, 2 or 3 standard deviations of the estimated mean derived from porcine USP Heparin, nor are any intermediates consistent with the intermediates required for bioequivalent heparin.

Further differences between the present invention and the prior art include, inter alia, the third intermediate NS2S6S, also called TriS. Certain prior methods that use chemical methods of sulfation cannot make an intermediate NS2S6S that lacks the 3S disaccharide. Certain chemoenzymatic methods did not control the major disaccharide group content in each chemoenzymatic step sufficient to obtain the NS2S6S intermediate.

In Bhaskar, U., et al (2015). *Carbohydrate Polymers*, 122, 399-407. the major disaccharide compositions such as NS6S, NS2S, NS2S6S of the pre-3OST intermediate are 7.8, 15.7, and 67.9% (w/w), respectively. The resulting "heparin" is not bioequivalent to porcine USP Heparin, and the disaccharide composition of the pre-3OST intermediate in this reference is unlike the third intermediate NS2S6S/TriS required for bioequivalent heparin. The highest anti-IIa activity reported for the "heparin" prepared in this reference was 151 U/mg, which is less than the required 180 U/mg, making it non-equivalent to porcine USP Heparin. In addition, the molecular weight of the product prepared by Bhaskar et al. was >25,000 dal.

In Zhang, Z., et al (2008) *Journal of the American Chemical Society*, 130(39), 12998-13007, the "Heparin", a counterpart of the third intermediate NS2S6S, does not contain the N-acetyl group that represents OS, 2S, 6S, and 2S6S. The resulting "heparin" is not bioequivalent to porcine USP Heparin, and the disaccharides of the pre-3OST intermediate in this reference cannot meet the requirements of the third intermediate NS2S6S required for bioequivalent heparin. The activity of this heparin was determined to be 180 U/mg by the clot-based activated partial thromboplastin time (APTT) assay. This assay is not equivalent to the anti-IIa activity described in the current USP so that it is unclear whether this would meet the activity specifications for porcine USP Heparin. Furthermore, no anti-Xa assay was performed in this study so that an anti-Xa/anti-IIa ratio of this "heparin" is not defined. In summary, in the absence of an N-acetyl group and no defined anti-IIa and anti-Xa activities, this heparin is not bioequivalent to porcine USP Heparin.

*J Med Chem* 48(2): 349-352 (2005), shows a molecule "neoheparin" with a molecular weight of approximately 8,000; anti-Xa 162; anti-IIa 62; anti-Xa/anti IIa 2.6, i.e. nonbioequivalent. Considering the gap of molecular weight and anticoagulation activity of post 3OST reaction in the chemoenzymatic procedure between neoheparin and bioequivalent heparin, the pre-3OST intermediate of neoheparin is unlike the third intermediate NS2S6S required for bioequivalent heparin.

U.S. Pat. No. 6,162,797 provides a heparin derivative obtained by step-wise chemical sulfation of epimerized N-deacetylated, N-sulfated heparosan. However, this derivative has anti-Xa 500-600, anti-IIa 250-320 (although in the specification "APTT" was used instead of anti-IIa, and it is highly likely "APTT" should have been anti-IIa), i.e. not bioequivalent. It follows that this document does not teach or suggest an intermediate equivalent to the third intermediate NS2S6S required for bioequivalent heparin. This patent also does not teach the first (NS) intermediate or the second intermediate disclosed below.

US 2014/0349962 A1 shows a heparin derivative, "Mitrin", obtained by chemoenzymatic functionalization of heparosan. "Mitrin" is hexasaccharide free of the 2-0 sulfated iduronic acid group with higher anti Xa activity than USA heparin. Therefore, this document does not teach or suggest the second intermediate (NS2S) or an intermediate equivalent to the third intermediate (NS2S6S).

Thus, while "biosynthetic heparins" described in the above references share some properties with porcine USP Heparin, they are not chemically equivalent or bioequivalent to porcine USP Heparin. The above references also do not teach or suggest what factors are missing, what steps to alter or how to alter them, to make biosynthetic heparin. The biosynthetic heparin intermediates described herein are not found in the intermediates of heparin production in vivo. In particular, natural heparin intermediates are bound to a proteoglycan linker, (Sugahara K, Kitagawa H. (2002) Heparin and heparan sulfate biosynthesis. *IUBMB Life*, 54(4): 163-75), and hence, do not exist in the free form with the specifications given in the current invention. Thus, the biosynthetic heparin is not a natural product.

The present inventors have generated biosynthetic heparin, which may be bioequivalent to porcine USP Heparin. The inventors have elucidated three intermediates, which may be essential to the synthesis of heparin, which is bioequivalent to porcine USP Heparin, through chemoenzymatic procedures from heparosan. These intermediates, which are labeled below according to their dominant disaccharide groups as an NS intermediate, an NS2S intermediate, and an NS2S6S intermediate (or a TriS intermediate), are characterized by specific ranges of modified sugar species, such as disaccharide groups. They may further be characterized by molecular weight properties and distributions. These intermediates may not have antithrombin-mediated anticoagulant activities.

The present disclosure concerns the synthesis of biosynthetic heparin from heparosan, such as derived from the bacterial exopolysaccharide heparosan, and the elucidation of properties of the key intermediates, which may be necessary to obtain bioequivalent heparin. In some embodiments, the biosynthetic heparin may meet US Pharmacopeia (USP) requirements for activity, specifically anticoagulant activity of heparin on factor IIa (i.e. anti-IIa) of not less or greater than 180 U/mg, and the ratio of activity on factor Xa to factor IIa (i.e. anti-Xa/anti-IIa) is between 0.85-1.15 or 0.9 and 1.1 or about 1.0. The biosynthetic heparin may also meet USP requirements for molecular weight distribution: a weight average of 15,000-19,000 Da; the percentage of heparin chains with a molecular weight of greater than 24,000 Da are not more than 20% of the total (herein including 0-15%, 0-10%, and 5-10%); and the ratio of chains between molecular weights of 8,000 to 16,000 Da to chains between molecular weights of 16,000 to 24,000 Da is not less than 1.0 (herein including between 1.0 to 2.5; 1.0 to 2.0, 1.2 to 1.8, 1.4-1.7, 1.5, or 1.6). Thus, the biosynthetic heparin may be bioequivalent to porcine USP Heparin.

In one embodiment, the first intermediate NS may be a glycosaminoglycan material comprising an effective amount of N-sulfated (NS) disaccharide groups. For example, N-sulfated (NS) disaccharide groups may constitute 78-99.5% or 78-99% or 81-97% or 83-95% or 84-94% or 85-93% or 84-87% or 85-86% or 87.5-94% or 90-93.5% or 90.5-93% or 90.3-91.3% or 92.2-93.2% or any value or subrange within these ranges of the first intermediate NS. In some related embodiments, the remainder of the first intermediate NS may be minor unmodified N-acetylated glucosamine (NAc) (OS) disaccharide group. In all cases, the NS must contain some measurable NAc groups.

The molecular weight properties of the first intermediate may be appropriate for forming a biosynthetic heparin that may meet molecular weight specifications for porcine USP Heparin Sodium using, for example, one of the methods disclosed below.

In some embodiments, the first intermediate NS is a glycosaminoglycan material comprising 84.7-93.8 weight % N-sulfated (NS) disaccharide groups. In related embodiments, the remainder is minor unmodified N-acetylated glucosamine (NAc) (OS) disaccharide group.

In some embodiments, the first intermediate NS may include 83.4-87.4% or 83.9-86.9% or 84.4-86.4% or 84.9-85.9% or any value or subrange within these ranges of NS disaccharide groups. The remainder of such first intermediate NS may be minor unmodified N-acetylated glucosamine (NAc) (OS) disaccharide group.

In some embodiments, the first intermediate NS may include from 87.9% to 92.9% or from 88.4% to 92.4% or from 88.9% to 91.9% or from 89.4% to 91.4% or from 89.9% to 90.9% or any value or subrange within these ranges of NS disaccharide groups. The remainder of such first intermediate NS may be minor unmodified N-acetylated glucosamine (NAc) (OS) disaccharide group.

In some embodiments, the first intermediate NS may include 88.8-94.7% or 89.3%-94.2% or 89.8-93.7% or 90.3%-93.2% or any value or subrange within these ranges of NS disaccharide groups. The remainder of such first intermediate NS may be minor unmodified N-acetylated glucosamine (NAc) (OS) disaccharide group.

In some embodiments, the first intermediate NS may include 88.8-92.8% or 89.3-92.3% or 89.8-91.8% or 90.3-91.3% or any value or subrange within these ranges of NS disaccharide groups. The remainder of such first intermediate NS may be minor unmodified N-acetylated glucosamine (NAc) (OS) disaccharide group.

In some embodiments, the first intermediate may include 90.1-94.7% or 90.6-94.2% or 91.1%-93.7% or 91.6%-93.2% or any value or subrange within these ranges of NS disaccharide groups. The remainder of such first intermediate NS may be minor unmodified N-acetylated glucosamine (NAc) (OS) disaccharide group.

Another embodiment may be a glycosaminoglycan second intermediate NS2S, which may be a glycosaminoglycan material comprising an effective amount of N-sulfated, 2-O-sulfated (NS2S) disaccharide group. For example, in some embodiments, N-sulfated, 2-O-sulfated (NS2S) disaccharide group may constitute 44-80% or 45-79% or 50-78% or 50-77% or 55-78% or 55-76% or 58-77% or 59-76% or 60-75% or 58-62% or 59-61% or 65-77% any value or subrange within these ranges of the glycosaminoglycan second intermediate NS2S.

The glycosaminoglycan second intermediate NS2S may also comprise NS disaccharide group in addition to the N-sulfated, 2-O-sulfated (NS2S) disaccharide group. For example, the NS disaccharide group may constitute 12-40% or 13-39% or 15-34% or 15-29% or 16-29% or 16-26% or 17-25% or 16-18% or 19-26% or any value or subrange within these ranges of the glycosaminoglycan second intermediate NS2S. Each of the ranges for the NS disaccharide group may be used with each of the above ranges for the N-sulfated, 2-O-sulfated (NS2S) disaccharide group.

In addition to the N-sulfated, 2-0-sulfated (NS2S) disaccharide group and the NS disaccharide group, the glycosaminoglycan second intermediate NS2S may also include one or more of minor unmodified N-acetylated glucosamine (NAc) (OS) disaccharide group and 2-O-sulfated, NAc (2S) disaccharide group. In certain embodiments, the only components of the glycosaminoglycan second intermediate NS2S other than the N-sulfated, 2-O-sulfated (NS2S) disaccharide group and the N-sulfated, 2-O-sulfated (NS2S) disaccharide group may be minor unmodified N-acetylated glucosamine (NAc) (OS) disaccharide group and/or 2-O-sulfated, NAc (2S) disaccharide group. In some embodiments, the combined amount of OS and 2S disaccharide groups may be 0.4-25% or 4-24% or 5-24% or 6-20% or 6-18% or 6-16% or 7-23% or 7-20% or 7-17% or 7-15% of the second intermediate NS2S.

The molecular weight properties of the second intermediate may be appropriate for forming a biosynthetic heparin that may meet molecular weight specifications for porcine USP Heparin Sodium using, for example, one of the methods disclosed below.

In some embodiments, the glycosaminoglycan second intermediate NS2S may comprise 73.8-75.3 weight % N-sulfated, 2-O-sulfated (NS2S) disaccharide group, and 18.5-20.2 weight % NS disaccharide group. The remainder of the glycosaminoglycan second intermediate NS2S may comprise, or consist of minor unmodified N-acetylated glucosamine (NAc) (OS) disaccharide group and 2-O-sulfated, NAc (2S) disaccharide group.

In some embodiments, the glycosaminoglycan second intermediate NS2S may comprise 57.5-62.5% or 58-62% or 58.5-61.5% or 59-61% or 59.5-60.5% or value or subrange within these ranges of NS2S disaccharide groups. In addition, the glycosaminoglycan second intermediate NS2S may comprise 23.2-27.2% or 23.7-26.7% or 24.2-26.2% or 24.7-25.7% or any value or subrange within these ranges of NS disaccharide groups. The remainder of the glycosaminoglycan second intermediate NS2S may comprise, or consist of minor unmodified N-acetylated glucosamine (NAc) (OS) disaccharide group and/or 2-O-sulfated, NAc (2S) disaccharide group. The combined amount of OS and 2S groups may constitute from 13.3-16.3% or 13.8-15.8% or 14.3-15.3% of the second intermediate.

In some embodiments, the glycosaminoglycan second intermediate NS2S may comprise 65.8-77.4% or 66.3-76.9% or 66.8-76.4% or 67.3-75.9% or value or subrange within these ranges of NS2S disaccharide groups. In addition, the glycosaminoglycan second intermediate NS2S may comprise 14.8-26% or 15.3-25.5% or 15.8-25% or 16.3-24.5% or any value or subrange within these ranges of NS disaccharide groups. The remainder of the glycosaminoglycan second intermediate NS2S may comprise, or consist of minor unmodified N-acetylated glucosamine (NAc) (OS) disaccharide group and/or 2-O-sulfated, NAc (2S) disaccharide group. The combined amount of OS and 2S groups may constitute from 5.6-10.8% or 6.1-10.3% or 6.6-9.8% of the second intermediate.

In some embodiments, the glycosaminoglycan second intermediate NS2S may comprise 65.8-74.4% or 66.3-73.9% or 66.8-73.4% or 67.3-72.9% or value or subrange within these ranges of NS2S disaccharide groups. In addition, the glycosaminoglycan second intermediate NS2S may comprise 17.9-26% or 18.4-25.5% or 18.9-25% or 19.4-24.5% or any value or subrange within these ranges of NS disaccharide groups. The remainder of the glycosaminoglycan second intermediate NS2S may comprise, or consist of minor unmodified N-acetylated glucosamine (NAc) (OS) disaccharide group and/or 2-O-sulfated, NAc (2S) disaccharide group. The combined amount of OS and 2S groups may constitute from 5.6-10.8% or 6.1-10.3% or 6.6-9.8% of the second intermediate.

In some embodiments, the glycosaminoglycan second intermediate NS2S may comprise 73.4-77.4% or 73.9-76.9% or 74.4-76.4% or 74.9-75.9% or value or subrange within these ranges of NS2S disaccharide groups. In addition, the glycosaminoglycan second intermediate NS2S may comprise 14.8-18.8% or 15.3-18.3% or 15.8-17.8% or 16.3-17.3% or any value or subrange within these ranges of NS disaccharide groups. The remainder of the glycosaminoglycan second intermediate NS2S may comprise, or consist of minor unmodified N-acetylated glucosamine (NAc) (OS) disaccharide group and/or 2-O-sulfated, NAc (2S) disaccharide group. The combined amount of OS and 2S groups may constitute from 5.8-9.8% or 6.3-9.3% or 6.8-8.8% of the second intermediate.

The second intermediate may be appropriate to form heparin with size and activity requirements consistent with porcine USP Heparin. In other words, the second intermediate may be such that heparin with size and activity requirements consistent with porcine USP Heparin Sodium may be formed using, for example, one of the methods disclosed below. For example, the second intermediate may have a weight average molecular weight appropriate to form a final heparin product with size and activity requirements consistent with porcine USP Heparin Sodium. The effective amount of N-sulfated, 2-O-sulfated (NS2S) disaccharide groups in the second intermediate may be such that heparin with size and activity requirements consistent with porcine USP Heparin Sodium may be formed using, for example, one of the methods disclosed below.

Another embodiment is a glycosaminoglycan third intermediate NS2S6S that may be a glycosaminoglycan material comprising effective amounts of N-sulfated, 2-O-sulfated, 6-O-sulfated (NS2S6S or also known as TriS) disaccharide group and N-sulfated, 6-O-sulfated (NS6S) disaccharide group. For example, NS2S6S disaccharide group may constitute 30-74% or 31-73% or 36-70% or 40-67% or 40-66% or 42-65% or 44-64% or 42-45% or 48-65% or any value or subrange within these ranges of the glycosaminoglycan third intermediate NS2S6S. NS6S disaccharide group may constitute 5-40% or 5-32% or 5-26% or 5-23% or 5-7% or 8-16% or 18-23% or 6-69% or 6-32% or 6-26% or 6-21% or any value or subrange within these ranges of the glycosaminoglycan third intermediate NS2S6S. Each of the ranges for NS6S disaccharide group may be used with each of the above ranges for NS2S6S disaccharide group.

Preferably, the glycosaminoglycan third intermediate NS2S6S does not contain 3S disaccharide groups.

In addition to the NS2S6S and NS6S disaccharide groups, the glycosaminoglycan third intermediate NS2S6S may also comprise N-sulfated, 2-O-sulfated (NS2S) disaccharide group and/or NS disaccharide group. The NS2S disaccharide group may constitute 1-28% or 1-27% or 4-28% or 8-28% or 10-28% or 11-28% or 12-27% or 11-22% or 19-27% or 3-23% or 5-19% or 7-16% or any value or subrange within these ranges of the glycosaminoglycan third intermediate NS2S6S. The NS disaccharide group may constitute 0.5-23% or 0.5-20% or 0.5-19% or 0.5-18% or 0.5-17% or 1-21% or 1-19% or 1-18% or 1-17% or 1-15% or any value or subrange within these ranges of the glycosaminoglycan third intermediate NS2S6S.

Besides the NS2S6S, NS6S, NS2S and NS disaccharide groups, the glycosaminoglycan third intermediate NS2S6S may comprise one or more of OS, 2S, 6-0-sulfated, NAc (6S) and 2-O-sulfated, 6-0-sulfated, NAc (2S6S) disaccharide groups. In certain embodiments, the only components of the glycosaminoglycan third intermediate NS2S6S may be (a) OS; (b) 6S; (c) 2S; and/or (d) 2S6S. The total amount of (a) OS; (b) 6S; (c) 2S; and/or (d) 2S6S in the glycosaminoglycan third intermediate NS2S6S may be, for example, 28% or less or 27% or less or 23% or 19% or 16%. In some embodiments, the combined amount of (a) OS; (b) 6S; (c) 2S; and (d) 2S6S in the glycosaminoglycan third intermediate NS2S6S may be 0.5-28% or 1-27% or 2-24% or 3-23% or 4-20% or 5-19% or 8-17% or 7-16% or any value or subranges within these ranges.

In some embodiments, the third intermediate may comprise 57.4-62.0 weight % (53.3-59.4 mol %) N-sulfated, 2-O-sulfated, 6-0-sulfated (NS2S6S or also known as TriS) disaccharide group, 17.7-22.2 weight % (10.6-15.1 mol %) N-sulfated, 6-0-sulfated (NS6S) disaccharide group, 8.4-10.9 weight % (12.0-13.8 mol %) N-sulfated, 2-O-sulfated (NS2S) disaccharide group, and 3.1-8.1 weight % (5.0-12.2 mol %) NS disaccharide group. In related embodiments, the remainder may comprise, or consist, of OS, 2S, 6-O-sulfated, NAc (6S) and 2-O-sulfated, 6-O-sulfated, NAc (2S6S) disaccharide groups. In a further embodiment, the third intermediate (NS2S6S) comprises no more than 10 weight % of total minor disaccharide sequences selected from (a) OS; (b) 6S; (c) 2S; and/or (d) 2S6S. Preferably, such third intermediate does not contain 3S disaccharide groups.

In some embodiments, the third intermediate may comprise 41.5-45.5% or 42-45% or 42.5-44.5% or 43-44% of NS2S6S disaccharide group, 8.5-12.5% or 9-12% or 9.5-11.5% 10-11% of NS6S disaccharide group, 12-15% or 12.5-14.5% or 13-14% of NS2S disaccharide group and 14.6-18.6% or 15.1-18.1% or 15.6-17.6% or 16.1-17.1% of NS disaccharide group. The remainder may comprise or consist of one or more of OS; (b) 6S; (c) 2S; and (d) 2S6S. The combined amount of the OS, 6S, 2S and/or 2S6S groups in the third intermediate may constitute 14.4-17.4% or 14.9-16.9% or 15.4-16.4% of the third intermediate. Preferably, such third intermediate does not contain 3S disaccharide groups.

In some embodiments, the third intermediate may comprise 51.3-60.3% or 51.8-59.8% or 52.3-59.3% or 52.8-58.8% of NS2S6S disaccharide group, 8.6-13.5% or 9.1-13% or 9.6-12.5% or 10.1-12% of NS6S disaccharide group, 10-15.8% or 10.5-15.3% or 11-14.8% or 11.5-14.3% of NS2S disaccharide group and 7.4-15.2% or 7.9-14.7% or 8.4-14.2% or 8.9-13.7% or 8.9-9.9% or 11.7-13.7% of NS disaccharide group. The remainder may comprise or consist of one or more of OS; (b) 6S; (c) 2S; and (d) 2S6S. In some embodiments, 2S6S groups may not be present in the third intermediate. The combined amount of the OS, 6S, 2S and/or 2S6S groups in the third intermediate may constitute 7.3-11.6% or 7.8-11.1% or 8.3-10.6% of the third intermediate. Preferably, such third intermediate does not contain 3S disaccharide groups.

In some embodiments, the third intermediate may comprise 41.5-65.7% or 42-65.2% or 42.5%-64.7% or 43-64.2% of NS2S6S disaccharide group, 4.1-23.3% or 4.6-22.8% or 5.1%-22.3% or 5.6-21.8% of NS6S disaccharide group, 10-28.6% 10.5-28.1% or 11-27.6% or 11.5-27.1% or 11.1-17.8% or 19-27.6% of NS2S disaccharide group and 0.4-15.9% or 0.7-15.4% or 1-14.9% or 1-14.4% or 0.4-5.5% or 10.2-14.9% of NS disaccharide group. The remainder may comprise or consist of one or more of OS; (b) 6S; (c) 2S; and (d) 2S6S. In some embodiments, 2S6S groups may not be present in the third intermediate. The combined amount of the OS, 6S, 2S and/or 2S6S groups in the third intermediate may constitute 5.3-9.7% or 5.8-9.2% or 6.3-8.7% of the third intermediate. Preferably, such third intermediate does not contain 3S disaccharide groups.

The molecular weight properties of the third intermediate may be appropriate for forming a biosynthetic heparin that may meet molecular weight specifications for porcine USP Heparin using, for example, one of the methods disclosed below.

The third intermediate may be appropriate to form heparin with size and activity requirements consistent with porcine USP Heparin. In other words, the third intermediate may be such that heparin with size and activity requirements consistent with porcine USP Heparin may be formed. For example, the third intermediate may have weight average molecular weight appropriate to form a final heparin product with size and activity requirements consistent with porcine USP Heparin. In other words, the third intermediate may be such that heparin with size and activity requirements consistent with porcine USP Heparin may be formed. The effective amounts of NS2S6S and NS6S disaccharide groups in the third intermediate may be such that heparin with size and activity requirements consistent with USP heparin may be formed.

It may be possible that none of the first, the second and the third intermediates possesses anticoagulant activity. None of these intermediates may be found in nature. The present applicants have been able to obtain heparin, which may be bioequivalent USP heparin with size and activity requirements consistent with porcine USP heparin using the above disclosed three intermediates.

Methods of making heparin, which may be bioequivalent to porcine USP heparin, are also provided.

One embodiment may be a method of producing heparin, which may be bioequivalent to porcine USP Heparin, from the third intermediate NS2S6S. In certain embodiments, the method may comprise:

(a) obtaining a glycosaminoglycan third intermediate NS2S6S as disclosed above; and (b) treating the third intermediate NS2S6S with 3-O-sulfotransferase isoform 1 (3OST-1) in the presence of a sulfate donor, such as 3'-phosphoadenosine 5'-phosphosulfate (PAPS) to produce heparin, which may be bioequivalent to porcine USP Heparin Sodium.

In some embodiments, the treatment of the third intermediate NS2S6S may be performed in the presence of a PAPS recycling system, which may comprise p-nitrophenylsulphate (PNPS) and PAPS. The PAPS recycling system may further comprise a catalyst, such as aryl sulfotransferase IV (AST-IV), which may be used to catalyze the conversion of PAP to PAPS using p-nitrophenylsulfate (PNPS) as sulfate donor with sufficient PNPS in the reaction based on the molar conversion of the third intermediate NS2S6S by 3OST-I enzyme. In some embodiments, the treatment may be performed without a PAPS recycling system with sufficient PAPS in the reaction based on the molar conversion of the third intermediate NS2S6S by 3OST-I enzyme. In some embodiments, the treatment may be performed in a buffer a 2-(N-morpholino)ethanesulfonic acid (MES) reaction buffer in the presence of the 3OST-I enzyme. Other suitable buffers and buffer concentrations as known to those in the art, such as phosphate buffer, may be used. A sulfate donor, such as PAPS or PAP plus PNPS, may be present. The buffer may have a pH of 7.0-7.4, such as about 7.2. The treatment may be performed at an elevated temperature, such as 30-45° C. or 33-42° C. or 35-40° C. Preferably, for the treatment, fresh enzymes, such as 3OST-I are used. The enzymes may be immobilized or in solution. Following the treatment, the product of the treatment containing the biosynthetic heparin may be purified to remove post-reaction compounds, such as PAP, PAPS, PNPS and/or PNP. In some embodiments, the produced biosynthetic heparin may be purified using a chromatographic method such as Strong Anion Exchange chromatography, which may contain an anion exchange resin, such as for example, Q Sepharose resin. The produced biosynthetic heparin may be bound to such resin in a salt solution, which may be for example, a NaCl solution. The purified biosynthetic heparin may then be desalted and concentrated.

In some embodiments, if the desired activity, an anticoagulant activity and/or anti-IIa activity, is not achieved in the produced heparin, the treatment may be repeated to produce heparin with the desired activity. For example, the initially produced heparin may have a ratio of activity on factor Xa to factor II (i.e. anti-Xa/anti-IIa) below 0.9, such as a value in 0.6-0.9 or 0.7-0.9, or above 1.1, such as a value in 1.1-1.5 or 1.1-1.4 or 1.1-1.3 or 1.1-1.2 ranges, the treatment with 3OST-1 may be repeated to produced heparin with a ratio of activity on factor Xa to factor IIa (i.e. anti-Xa/anti-IIa) of 0.9-1.1 or about 1.0.

For example, in some embodiments, the method may comprise:

(a) obtaining a glycosaminoglycan, which preferably does not contain 3S disaccharide groups, while comprising:

(i) 57.4-62.0 weight % N-sulfated, 2-sulfated, 6-sulfated (TriS) disaccharide group;

(ii) 17.7-22.2 weight % N-sulfated, 6-sulfated (NS6S) disaccharide group;

(iii) 8.4-10.9 weight % N-sulfated, 2-sulfated (NS2S) disaccharide group; and (iv) 3.1-8.1 weight % N-sulfated (NS) disaccharide group; and (v) optionally, the combination of N-acetylated glucosamine residue containing minor disaccharide groups OS, 2S, 6S, and 2S6S comprising the balance;

(b) treating the glycosaminoglycan with 3-0-sulfotransferase isoform 1 (3OST-1) in the presence of a sulfate donor, such as of 3'-phosphoadenosine 5'-phosphosulfate (PAPS) to generate biosynthetic heparin, which may be bioequivalent to USP heparin. In step (b) sufficient glucosamine residues may be converted to 3-O-sulfoglucosamine residues to obtain a heparin, which may have anti-IIa activities of not less or greater than 180 units/mg and an anti-Xa/anti-IIa ratio of 0.85-1.15 or 0.9-1.1 or about 1.0.

In some embodiments, the method may comprise:

(a) obtaining a glycosaminoglycan, which preferably does not contain 3S disaccharide groups, while comprising:

(i) 30-74% or 31-73% or 36-70% or 40-67% or 40-66% or 42-65% or 44-64% or 42-45% or 48-65% of NS2S6S disaccharide group, (ii) 5-40% or 5-32% or 5-26% or 5-23% or 5-7% or 8-16% or 18-23% or 6-39% or 6-32% or 6-26% or 6-21% of NS6S disaccharide group, (iii) 1-28% or 1-27% or 4-28% or 4-27% or 8-28% or 8-27% or 10-28% or 11-28% or 12-27% or 11-22% or 19-27% of NS2S disaccharide group, (iv) 0.5-23% or 0.5-20% or 0.5-19% or 0.5-18% or 0.5-17% or 1-21% or 1-19% or 1-18% or 1-17% or 1-15% of NS disaccharide group, and (v) optionally, one or more disaccharide groups OS, 2S, 6S, and 2S6S comprising the remainder of the glycosaminoglycan;

(b) treating the glycosaminoglycan with 3-0-sulfotransferase isoform 1 (3OST-1) in the presence of a sulfate donor, such as 3'-phosphoadenosine 5'-phosphosulfate (PAPS) to generate biosynthetic heparin, which may be bioequivalent to USP heparin. In step (b) sufficient glucosamine residues may be converted to 3-O-sulfoglucosamine residues to obtain a heparin, which may have anti-IIa activities of not less or greater than 180 units/mg and an anti-Xa/anti-IIa ratio of 0.85-1.15 or 0.9-1.1 or about 1.0.

In some embodiments, the method may comprise:

(a) obtaining a glycosaminoglycan, which preferably does not contain 3S disaccharide groups, while comprising:

(i) 41.5-45.5% or 42-45% or 42.5-44.5% or 43-44% of NS2S6S disaccharide group, (ii) 8.5-12.5% or 9-12% or 9.5-11.5% 10-11% of NS6S disaccharide group, (iii) 12-15% or 12.5-14.5% or 13-14% of NS2S disaccharide group, (iv) 14.6-18.6% or 15.1-18.1% or 15.6-17.6% or 16.1-17.1% of NS disaccharide group and (v) optionally, one or more groups OS, 2S, 6S, and 2S6S comprising the remainder of the glycosaminoglycan;

(b) treating the glycosaminoglycan with 3-O-sulfotransferase isoform 1 (3OST-1) in the presence of a sulfate donor, such as 3'-phosphoadenosine 5'-phosphosulfate (PAPS) to generate biosynthetic heparin, which may be bioequivalent to USP heparin. In step (b) sufficient glucosamine residues may be converted to 3-O-sulfoglucosamine residues to obtain a heparin, which may have anti-IIa activities of not less or greater than 180 units/mg and an anti-Xa/anti-IIa ratio of 0.85-1.15 or 0.9-1.1 or about 1.0.

In some embodiments, the method may comprise:

(a) obtaining a glycosaminoglycan, which preferably does not contain 3S disaccharide groups, while comprising:

(i) 51.3-60.3% or 51.8-59.8% or 52.3-59.3% or 52.8-58.8% of NS2S6S disaccharide group, (ii) 8.6-13.5% or 9.1-13% or 9.6-12.5% or 10.1-12% of NS6S disaccharide group, (iii) 10-15.8% or 10.5-15.3% or 11-14.8% or 11.5-14.3% of NS2S disaccharide group, (iv) 7.4-15.2% or 7.9-14.7% or 8.4-14.2% or 8.9-13.7% or 8.9-9.9% or 11.7-13.7% of NS disaccharide group and (v) optionally, one or more disaccharide groups OS, 2S, 6S, and 2S6S comprising the remainder of the glycosaminoglycan;

(b) treating the third intermediate NS2S6S with 3-O-sulfotransferase isoform 1 (3OST-1) in the presence of a sulfate donor, such as 3'-phosphoadenosine 5'-phosphosulfate (PAPS) to generate biosynthetic heparin, which may be bioequivalent to USP heparin. In step (b) sufficient glucosamine residues may be converted to 3-O-sulfoglucosamine residues to obtain a heparin, which may have anti-IIa activities of not less or greater than 180 units/mg and an anti-Xa/anti-IIa ratio of 0.85-1.15 or 0.9-1.1 or about 1.0.

In some embodiments, the method may comprise:

(a) obtaining a glycosaminoglycan which preferably does not contain 3S disaccharide groups, while comprising:

(i) 41.5-65.7% or 42-65.2% or 42.5%-64.7% or 43-64.2% of NS2S6S disaccharide group, (ii) 4.1-23.3% or 4.6-22.8% or 5.1%-22.3% or 5.6-21.8% of NS6S disaccharide group, (iii) 10-28.6% 10.5-28.1% or 11-27.6% or 11.5-27.1% or 11.1-17.8% or 19-27.6% of NS2S disaccharide group, (iv) 0.4-15.9% or 0.7-15.4% or 1-14.9% or 1-14.4% or 0.4-5.5% or 10.2-14.9% of NS disaccharide group and (v) optionally, one or more disaccharide groups OS, 2S, 6S, and 2S6S comprising the remainder of the glycosaminoglycan;

(b) treating the glycosaminoglycan with 3-O-sulfotransferase isoform 1 (3OST-1) in the presence of a sulfate donor, such as 3'-phosphoadenosine 5'-phosphosulfate (PAPS) to generate biosynthetic heparin, which may be bioequivalent to USP heparin. In step (b) sufficient glucosamine residues may be converted to 3-O-sulfoglucosamine residues to obtain a heparin, which may have anti-IIa activities of not less or greater than 180 units/mg and an anti-Xa/anti-IIa ratio of 0.85-1.15 or 0.9-1.1 or about 1.0.

Another embodiment may be a method of making a first intermediate NS as disclosed above. The method may comprise obtaining heparosan and then converting an amount of the N-acetyl glucosamine residues in the heparosan to N-sulfo glucosamine residues to produce the first intermediate NS. The converted amount of the N-acetyl glucosamine residues may correspond to an amount of N-sulfated (NS) disaccharide group in the first intermediate NS. In related embodiments, the first intermediate NS may be made from heparosan by reacting heparosan with chemical reagents, aqueous sodium hydroxide and a sulfonating reagent, such as triethylamine-sulfur trioxide complex, under the appropriate conditions to convert the N-acetyl glucosamine residues in heparosan to N-sulfo glucosamine residues to afford the first intermediate NS. In another embodiment, the first intermediate NS may be made from heparosan by reacting heparosan with an aqueous base solution, such as aqueous sodium hydroxide or aqueous potassium hydroxide, and N-sulfonating with phosphoadenosyl phosphosulfate (PAPS) using an N-sulfotransferase catalyst. The converted amount of the N-acetyl glucosamine residues may correspond to an amount of N-sulfated (NS) disaccharide group in the first intermediate NS. In another embodiment, heparosan may be reacted with N-deacetylase, N-sulfotransferase (NDST) to the N-acetyl glucosamine residues in heparosan to produce the first intermediate NS. The converted amount of the N-acetyl glucosamine residues may correspond to an amount of N-sulfated (NS) disaccharide group in the first intermediate NS. In each of the methods, it may be preferred that the number of unsubstituted amino groups remaining after either chemical or enzymatic N-sulfonation should be no greater than the number of unsubstituted amino groups found in porcine USP Heparin Sodium, one or fewer per chain (T. Toida, H. Yoshida, H. Toyoda, I. Koshiishi, T. Imanari, R. E. Hileman, J. R. Fromm, R. J. Linhardt, Biochemical Journal, 322, 499-506, 1997). The amount of the NS groups of the produced first intermediate may be controlled by controlling the chemical or enzymatic processes. (Z. Wang, et al. (2011), *Journal of Biotechnology*, 156, 188-196; A. Onishi (2015), Detailed physicochemical and biological analyses of heparins from various sources, PhD dissertation, Rensselaer Polytechnic Institute, Troy, N.Y., USA).

The molecular weight properties of the first produced intermediate may be such that they are appropriate for forming a biosynthetic heparin that may meet molecular weight specifications for porcine USP Heparin using, for example, one of the methods disclosed below.

Heparosan used in the methods of the present disclosure may be, for example, heparosan produced using bacteria, such as *Escherichia coli* (*E. coli*) or *Pasteurella multocida*. For example, heparosan may be produced from *E. coli* K5 or *E. coli* Nissle 1917. Prior to production of the first intermediate, the heparosan may be N-deacetylated and depolymerized as disclosed, for example, in Z. Wang et al (2011), *Journal of Biotechnology*, 156, 188-196.

In some embodiments, the method may be a method of making a first intermediate NS comprising 84.7-93.8 weight % N-sulfated (NS) disaccharide group. The remainder of the first intermediate NS may be minor unmodified N-acetylated glucosamine (NAc) (OS) disaccharide group. The method may comprise converting 84.7-93.8 weight % of the N-acetyl glucosamine residues in heparosan to produce a N-deacetylated, N-sulfated heparosan. In related embodiments, the first intermediate NS may be made from heparosan by reacting heparosan with chemical reagents, aqueous sodium hydroxide and a sulfonating reagent such as triethylamine-sulfur trioxide complex under the appropriate conditions to convert 84.7- 93.8 weight % of the N-acetyl glucosamine residues in heparosan to N-sulfo glucosamine residues to afford the first intermediate NS. Alternatively, heparosan may be reacted with N-deacetylase, N-sulfotransferase (NDST) to convert 84.7-93.8 weight % of the N-acetyl glucosamine residues in heparosan to produce the first intermediate NS.

In some embodiments, the method may be a method of making a first intermediate NS comprising 78-99.5% or 78-99% or 81-97% or 83-95% or 84-94% or 85-93% or 84-87% or 85-86% or 87.5-94% or 90-93.5% or 90.5-93% or 90.3-91.3% or 92.2-93.2% of N-sulfated (NS) disaccharide group. The remainder of the first intermediate NS may be minor unmodified N-acetylated glucosamine (NAc) (OS) disaccharide group. The method may comprise converting an amount of the N-acetyl glucosamine residues in heparosan, which amount corresponds to the amount of NS groups in the first intermediate, to produce a N-deacetylated, N-sulfated heparosan. In related embodiments, the first intermediate NS may be made from heparosan by reacting heparosan with chemical reagents, aqueous sodium hydroxide and a sulfonating reagent such as triethylamine-sulfur trioxide complex under the appropriate conditions to convert an amount of the N-acetyl glucosamine residues in heparosan, which amount corresponds to the amount of NS groups in the first intermediate, to N-sulfo glucosamine residues to afford the first intermediate NS. Alternatively, heparosan may be reacted with N-deacetylase, N-sulfotransferase (NDST) to convert an amount of the N-acetyl glucosamine residues in heparosan, which amount corresponds to the amount of NS groups in the first intermediate, to produce the first intermediate NS.

In some embodiments, the method may be a method of making a first intermediate NS comprising 83.4-87.4% or 83.9-86.9% or 84.4-86.4% or 84.9-85.9% of N-sulfated (NS) disaccharide group. The remainder of the first intermediate NS may be minor unmodified N-acetylated glucosamine (NAc) (OS) disaccharide group. The method may comprise converting an amount of the N-acetyl glucosamine residues in heparosan, which amount corresponds to the amount of NS groups in the first intermediate, to produce a N-deacetylated, N-sulfated heparosan. In related embodiments, the first intermediate NS may be made from heparosan by reacting heparosan with chemical reagents, aqueous sodium hydroxide and a sulfonating reagent such as triethylamine-sulfur trioxide complex under the appropriate conditions to convert an amount of the N-acetyl glucosamine residues in heparosan, which amount corresponds to the amount of NS groups in the first intermediate, to N-sulfo glucosamine residues to afford the first intermediate NS. Alternatively, heparosan may be reacted with N-deacetylase, N-sulfotransferase (NDST) to convert an amount of the N-acetyl glucosamine residues in heparosan, which amount corresponds to the amount of NS groups in the first intermediate, to produce the first intermediate NS. The produced first intermediate NS may have a weight average molecular weight that is sufficient to be converted through the process to give BSH with the appropriate molecular weight properties.

In some embodiments, the method may be a method of making a first intermediate NS comprising 87.9% to 92.9% or 88.4% to 92.4% or from 88.9% to 91.9% or from 89.4% to 91.4% or from 89.9% to 90.9% of N-sulfated (NS) disaccharide group. The remainder of the first intermediate NS may be minor unmodified N-acetylated glucosamine (NAc) (OS) disaccharide group. The method may comprise converting an amount of the N-acetyl glucosamine residues in heparosan, which amount corresponds to the amount of NS groups in the first intermediate, to produce a N-deacetylated, N-sulfated heparosan. In related embodiments, the first intermediate NS may be made from heparosan by reacting heparosan with chemical reagents, aqueous sodium hydroxide and a sulfonating reagent such as triethylamine-sulfur trioxide complex under the appropriate conditions to convert an amount of the N-acetyl glucosamine residues in heparosan, which amount corresponds to the amount of NS groups in the first intermediate, to N-sulfo glucosamine residues to afford the first intermediate NS. Alternatively, heparosan may be reacted with N-deacetylase, N-sulfotransferase (NDST) to convert an amount of the N-acetyl glucosamine residues in heparosan, which amount corresponds to the amount of NS groups in the first intermediate, to produce the first intermediate NS. The produced first intermediate NS may have a weight average molecular weight that is sufficient to be converted through the process to give BSH with the appropriate molecular weight properties.

In some embodiments, the method may be a method of making a first intermediate NS comprising 88.8-94.7% or 89.3%-94.2% or 89.8-93.7% or 90.3%-93.2% of N-sulfated (NS) disaccharide group. The remainder of the first intermediate NS may be minor unmodified N-acetylated glucosamine (NAc) (OS) disaccharide group. The method may comprise converting an amount of the N-acetyl glucosamine residues in heparosan, which amount corresponds to the amount of NS groups in the first intermediate, to produce a N-deacetylated, N-sulfated heparosan. In related embodiments, the first intermediate NS may be made from heparosan by reacting heparosan with chemical reagents, aqueous sodium hydroxide and a sulfonating reagent such as triethylamine-sulfur trioxide complex under the appropriate conditions to convert an amount of the N-acetyl glucosamine residues in heparosan, which amount corresponds to the amount of NS groups in the first intermediate, to N-sulfo glucosamine residues to afford the first intermediate NS. Alternatively, heparosan may be reacted with N-deacetylase, N-sulfotransferase (NDST) to convert an amount of the N-acetyl glucosamine residues in heparosan, which amount corresponds to the amount of NS groups in the first intermediate, to produce the first intermediate NS.

In some embodiments, the method may be a method of making a first intermediate NS comprising 88.8-92.8% or 89.3-92.3% or 89.8-91.8% or 90.3-91.3% of N-sulfated (NS) disaccharide group. The remainder of the first intermediate NS may be minor unmodified N-acetylated glucosamine (NAc) (OS) disaccharide group. The method may comprise converting an amount of the N-acetyl glucosamine residues in heparosan, which amount corresponds to the amount of NS groups in the first intermediate, to produce a N-deacetylated, N-sulfated heparosan. In related embodiments, the first intermediate NS may be made from heparosan by reacting heparosan with chemical reagents, aqueous sodium hydroxide and a sulfonating reagent such as triethylamine-sulfur trioxide complex under the appropriate conditions to convert an amount of the N-acetyl glucosamine residues in heparosan, which amount corresponds to the amount of NS groups in the first intermediate, to N-sulfo glucosamine residues to afford the first intermediate NS. Alternatively, heparosan may be reacted with N-deacetylase, N-sulfotransferase (NDST) to convert an amount of the N-acetyl glucosamine residues in heparosan, which amount corresponds to the amount of NS groups in the first intermediate, to produce the first intermediate NS.

In some embodiments, converting of heparosan into the first intermediate may involve obtaining or preparing a solution of heparosan. The solution may have a concentration from 0.05-12% or 0.1-10% or 0.1-5% or 0.1-3% or 0.5-2% of heparosan. The solvent may be, for example, water or a water based solvent. Thus, the solution may be an aqueous solution. The solution may be reacted with a base, such as sodium hydroxide or potassium hydroxide. The reaction may be performed at elevated temperature such as, for example, 30-70° C. or 40-65° C. or 50-55° C. Then an acid, such as, for example HCl, may be added to the reaction mixture to adjust pH to about 7. The product mat be exposed to N-sulfonation reaction, which may be performed, for example, using one or more N-sulfonation reagents, which may be, for example, sulfur trioxide or a sulfur sulfur trioxide complex, such as sulfur amine complex. Non-limiting examples of sulfur amine complexes include a sulfur trialkylamine complex, such as, for example, sulfur trimethylamine complex, sulfur trioxide dimethyl ethylamine complex, and sulfur trioxide methyl diethylamine complex, as well as sulfur trioxide-amine containing aryl complex, such as sulfur trioxide-pyridine complex. Then the product of the N-sulfonation may be fractionated to produce desired molecular weight properties.

In some embodiments, the method may be a method of making a first intermediate NS comprising 90.1-94.7% or 90.6-94.2% or 91.1%-93.7% or 91.6%-93.2% of N-sulfated (NS) disaccharide group. The remainder of the first intermediate NS may be minor unmodified N-acetylated glucosamine (NAc) (OS) disaccharide group. The method may comprise converting an amount of the N-acetyl glucosamine residues in heparosan, which amount corresponds to the amount of NS groups in the first intermediate, to produce a N-deacetylated, N-sulfated heparosan. In related embodiments, the first intermediate NS may be made from heparosan by reacting heparosan with chemical reagents, aqueous sodium hydroxide and a sulfonating reagent such as triethylamine-sulfur trioxide complex under the appropriate conditions to convert an amount of the N-acetyl glucosamine residues in heparosan, which amount corresponds to the amount of NS groups in the first intermediate, to N-sulfo glucosamine residues to afford the first intermediate NS. Alternatively, heparosan may be reacted with N-deacetylase, N-sulfotransferase (NDST) to convert an amount of the N-acetyl glucosamine residues in heparosan, which amount corresponds to the amount of NS groups in the first intermediate, to produce the first intermediate NS.

Another embodiment may be a method of making a second intermediate NS2S as disclosed above. The method may comprise (a) converting an amount of the N-acetyl glucosamine residues in heparosan to produce a first intermediate NS (the converted amount of the N-acetyl glucosamine residues may correspond to an amount of N-sulfated (NS) disaccharide group in the first intermediate NS) and then (b) treating the first intermediate NS with an enzyme, such as C5-epimerase (C5-epi) and/or 2-O-sulfotransferase (2OST), to produce the second intermediate NS2S. In some embodiemnts, the chain lengths or the second intermediate may be not appreciably different than the chain lengths of the first intermediate. Preferably, the treating involves both of C5-epi and 2OST enzymes.

The conversion of heparosan into the first intermediate may be performed as discussed above.

In some embodiments, the treatment may be performed in the presence of a PAPS recycling system, which may comprise p-nitrophenylsulphate (PNPS) and PAPS. The PAPS recycling system may further comprise a catalyst, such as aryl sulfotransferase IV (AST-IV), which may be used to catalyze the conversion of PAP to PAPS using PNPS as sulfate donor in the reaction based on the molar conversion of the first intermediate by C5-epi and 2OST enzymes. In some embodiments, the treatment may be performed without a PAPS recycling system but with suffiecient amount of PAPS in the reaction based on the molar conversion of the first intermediate NS2S6S. In some embodiments, the treatment may be performed, for example, in a buffer, such as 2-(N-morpholino)ethanesulfonic acid (MES) reaction buffer. Other suitable buffers and buffer concentrations as know to those skilled in the art may be used in the presence of C5 epi and 2OST enzymes. A sulfate donor, such as PAPS or PAP plus PNPS, may be present. The buffer may have a pH of 7.0-7.4, such as about 7.2. (The treatment may be performed at an elevated temperature, such as 30-45° C. or 33-42° C. or 35-40° C. Preferably, for the treatment, fresh enzymes, such as C5 epi and/or 2OST are used. The enzymes may be immobilized or in solution. Following the treatment, the product of the treatment containing the second intermediate may be purified to remove post-reaction compounds, such as PAP, PAPS, PNPS and/or PNP. The purified second intermediate may be collected and concentrated for further use, such as analysis and/or producing a third intermediate.

In some embodimens, if the desired disaccharide characteristics, such as a percentage of NS2S, is not achieved in the glycosaminoglycan produced as the result of the treatment, the treatment may be repeated to produce a glycosaminoglycan with disaccharide characteristics, such as a NS2S percentage desired for the second intermediate.

For example, in some embodiments, the method may be a method of making a second intermediate NS2S comprising 73.8-75.3 weight % N-sulfated, 2-O-sulfated (NS2S) disaccharide group, and 18.5-20.2 weight % NS disaccharide group. The remainder in the second intermediate NS2S may comprise, or consist of minor unmodified NAc (OS) disaccharide group and/or 2-O-sulfated, NAc (2S) disaccharide group. This method may comprise: (a) converting 84.7-93.8 weight % of the N-acetyl glucosamine residues in heparosan to produce the first intermediate NS; and (b) treating the first intermediate NS with an enzyme, such as C5-epimerase (C5-epi) and 2-O-sulfotransferase (2OST), in the presence of a sulfate donor, such as 3'-phosphoadenosine-5'-phosphosulfate (PAPS) to produce the second intermediate NS2S. Preferably, the treating involves both of C5-epi and 2OST enzymes.

In some embodiments, the method may be a method of making a second intermediate NS2S comprising 44-80% or 45-79% or 50-78% or 50-77% or 55-78% or 55-76% or 58-77% or 59-76% or 60-75% or 58-62% or 59-61% or 65-77% NS2S disaccharide groups and 12-40% or 13-39% or 15-34% or 15-29% or 16-29% or 17-25% or 16-26% or 16-18% or 19-26% of NS disaccharide groups. The remainder in the second intermediate NS2S may comprise, or consist of minor unmodified NAc (OS) disaccharide group and/or 2-O-sulfated, NAc (2S) disaccharide group. This method may comprise: (a) converting an amount of the N-acetyl glucosamine residues in heparosan to produce the first intermediate NS comprising 78-99.5% or 78-99% or 81-97% or 83-95% or 84-94% or 85-93% or 84-87% or 85-86% or 87.5-94% or 90-93.5% or 90.5-93% or 90.3-91.3% or 92.2-93.2% of N-sulfated (NS) disaccharide group (the converted amount of the N-acetyl glucosamine residues may correspond to the amount of NS groups in the first intermediate); and (b) treating the first intermediate NS with an enzyme, such as C5-epimerase (C5-epi) and 2-O-sulfotransferase (2OST), in the presence of a sulfate donor, such as 3'-phosphoadenosine-5'-phosphosulfate (PAPS), to produce the second intermediate NS2S. Preferably, the treating involves both of C5-epi and 2OST enzymes.

In some embodiments, the method may be a method of making a second intermediate NS2S comprising 57.5-62.5% or 58-62% or 58.5-61.5% or 59-61% or 59.5-60.5% of NS2S disaccharide groups and 23.2-27.2% or 23.7-26.7% or 24.2-26.2% or 24.7-25.7% of NS disaccharide groups. The remainder in the second intermediate NS2S may comprise, or consist of minor unmodified NAc (OS) disaccharide group and/or 2-O-sulfated, NAc (2S) disaccharide group. This method may comprise: (a) converting an amount of the N-acetyl glucosamine residues in heparosan to produce the first intermediate NS comprising 83.4-87.4% or 83.9-86.9% or 84.4-86.4% or 84.9-85.9% of N-sulfated (NS) disaccharide group (the converted amount of the N-acetyl glucosamine residues may correspond to the amount of NS groups in the first intermediate); and (b) treating the first intermediate NS with an enzyme, such as C5-epimerase (C5-epi) and 2-O-sulfotransferase (2OST), in the presence of a sulfate donor, such as 3'-phosphoadenosine-5'-phosphosulfate (PAPS) to produce the second intermediate NS2S. Preferably, the treating involves both of C5-epi and 2OST enzymes.

In some embodiments, the method may be a method of making a second intermediate NS2S comprising 65.8-77.4% or 66.3-76.9% or 66.8-76.4% or 67.3-75.9% of NS2S disaccharide groups and 14.8-26% or 15.3-25.5% or 15.8-25% or 16.3-24.5% of NS disaccharide groups. The remainder in the second intermediate NS2S may comprise, or consist of minor unmodified NAc (0S) disaccharide group and/or 2-O-sulfated, NAc (2S) disaccharide group. This method may comprise: (a) converting an amount of the N-acetyl glucosamine residues in heparosan to produce the first intermediate NS comprising from 88.8-94.7% or 89.3%-94.2% or 89.8-93.7% or 90.3%-93.2% of N-sulfated (NS) disaccharide group (the converted amount of the N-acetyl glucosamine residues may correspond to the amount of NS groups in the first intermediate); and (b) treating the first intermediate NS with an enzyme, such as C5-epimerase (C5-epi) and 2-O-sulfotransferase (2OST), in the presence of a sulfate donor, such as 3'-phosphoadenosine-5'-phosphosulfate (PAPS), to produce the second intermediate NS2S. Preferably, the treating involves both of C5-epi and 2OST enzymes.

In some embodiments, the method may be a method of making a second intermediate NS2S comprising 65.8-74.4% or 66.3-73.9% or 66.8-73.4% or 67.3-72.9% of NS2S disaccharide groups and 17.9-26% or 18.4-25.5% or 18.9-25% or 19.4-24.5% of NS disaccharide groups. The remainder in the second intermediate NS2S may comprise, or consist of minor unmodified NAc (0S) disaccharide group and/or 2-O-sulfated, NAc (2S) disaccharide group. This method may comprise: (a) converting an amount of the N-acetyl glucosamine residues in heparosan to produce the first intermediate NS comprising from 88.8-92.8% or 89.3-92.3% or 89.8-91.8% or 90.3-91.3% of N-sulfated (NS) disaccharide group (the converted amount of the N-acetyl glucosamine residues may correspond to the amount of NS groups in the first intermediate); and (b) treating the first intermediate NS with an enzyme, such as C5-epimerase (C5-epi) and 2-O-sulfotransferase (2OST), in the presence of a sulfate donor, such as 3'-phosphoadenosine-5'-phosphosulfate (PAPS), to produce the second intermediate NS2S. Preferably, the treating involves both of C5-epi and 2OST enzymes.

In some embodiments, the method may be a method of making a second intermediate NS2S comprising 73.4-77.4% or 73.9-76.9% or 74.4-76.4% or 74.9-75.9% of NS2S disaccharide groups and 14.8-18.8% or 15.3-18.3% or 15.8-17.8% or 16.3-17.3% of NS disaccharide groups. The remainder in the second intermediate NS2S may comprise, or consist of minor unmodified NAc (0S) disaccharide group and/or 2-O-sulfated, NAc (2S) disaccharide group. This method may comprise: (a) converting an amount of the N-acetyl glucosamine residues in heparosan to produce the first intermediate NS comprising from 90.1-94.7% or 90.6-94.2% or 91.1%-93.7% or 91.6%-93.2% of N-sulfated (NS) disaccharide group (the converted amount of the N-acetyl glucosamine residues may correspond to the amount of NS groups in the first intermediate); and (b) treating the first intermediate NS with an enzyme, such as C5-epimerase (C5-epi) and 2-O-sulfotransferase (2OST), in the presence of a sulfate donor, such as 3'-phosphoadenosine-5'-phosphosulfate (PAPS), to produce the second intermediate NS2S. Preferably, the treating involves both of C5-epi and 2OST enzymes.

Another embodiment may be a method of making a third intermediate NS2S6S as disclosed above. The method may comprise (a) converting an amount of the N-acetyl glucosamine residues in heparosan to produce a first intermediate NS (the converted amount of the N-acetyl glucosamine residues may correspond to an amount of N-sulfated (NS) disaccharide group in the first intermediate NS); (b) treating the first intermediate NS with an enzyme, such as C5-epimerase (C5-epi) and/or 2-O-sulfotransferase (2OST), in the presence of a sulfate donor, such as 3'-phosphoadenosine-5'-phosphosulfate (PAPS), to produce the second intermediate NS2S and (c) treating the second intermediate NS2S with an enzyme, such as 6-O-sulfotransferases 1 and 3 (6OST-1,3), in the presence of a sulfate donor, such as phosphoadenosyl phosphosulfate (PAPS), to produce the third intermediate NS2S6S.

The converting the heparosan to produce the first intermediate and the treatment of the first intermediate may be performed as disclosed above.

In some embodiments, the treatment may be performed in the presence of a PAPS recycling system, which may comprise p-nitrophenylsulphate (PNPS) and PAPS. The PAPS recycling system may further comprise a catalyst, such as aryl sulfotransferase IV (AST-IV), which may be used to catalyze the conversion of PAP to PAPS using PNPS as sulphate donor with a sufficient amount of PNPS in the reaction based on the molar conversion of the second intermediate by an enzyme, such as 6-O-sulfotransferases 1 and 3 (6OST-1,3). In some embodiments, the treatment may be performed without a PAPS recycling system but with a sufficient amount of PAPS in the reaction based on the molecular conversion of the second intermediate by an enzyme, such as 6-O-sulfotransferases 1 and 3 (6OST-1,3). In some embodiments, the treatment may be performed in a buffer, such as a 2-(N-morpholino)ethanesulfonic acid (MES) reaction buffer in the presence of 6OST-1 and 6OST-3 enzymes. A sulfate donor, such as PAPS or PAP plus PNPS, may be present. The buffer may have a pH of 7.0-7.4, such as about 7.2. The treatment may be performed at an elevated temperature, such as 30-45° C. or 33-42° C. or 35-40° C. Preferably, for the treatment, fresh enzymes, such as 6OST-1 and/or 6-OST-3 are used. The enzymes may be immobilized or in solution. Following the treatment, the product of the treatment containing the third intermediate may purified to remove post-reaction compounds, such as PAP, PAPS, PNPS and/or PNP. The purified third intermediate may be concentrated and collected for further use, such as analysis and/or producing a biosynthetic heparin.

In some embodiemnts, if desired dissachride characteristics, such as percentages of NS2S6S and NS6S, are not achieved in the glycosaminoglycan produced as the result of the treatment of the second intermediate NS, the treatment may be repeated to produce a glycosaminoglycan with disaccharide characteristics, such as NS2S6S and NS6S percentages desired for the third intermediate.

For example, in some embodiments, the method may be a method of making a third intermediate NS2S6S comprising 57.4-62.0 weight % N-sulfated, 2-O-sulfated, 6-O-sulfated (NS2S6S) disaccharide group, 17.7-22.2 weight % N-sulfated, 6-O-sulfated (NS6S) disaccharide group, 8.4-10.9 weight % N-sulfated, 2-O-sulfated (NS2S) disaccharide group, and 3.1-8.1 weight % NS disaccharide group. The remainder of the third intermediate NS2S6S may comprise, or consist of one or more of 0S, 2S, 6-O-sulfated, NAc (6S) 2-O-sulfated, 6-O-sulfated, NAc (2S6S) disaccharide groups. The third intermediate preferably does not contain 3S disaccharide groups. This method may comprise:

(a) converting 84.7-93.8 weight % of the N-acetyl glucosamine residues in heparosan to produce the first intermediate NS; (b) treating the first intermediate NS with an enzyme, such as C5-epimerase (C5-epi) and 2-O-sulfotransferase (2OST), in the presence of a sulfate donor, such as 3'-phosphoadenosine-5'-phosphosulfate (PAPS), to produce the second intermediate NS2S; and (c) treating the second intermediate NS2S with an enzyme, such as 6-O-sulfotransferases 1 and 3 (6OST-1,3), in the presence of a sulfate donor, such as phosphoadenosyl phosphosulfate (PAPS), to produce the third intermediate NS2S6S.

In some embodiments, the method may be a method of making a third intermediate NS2S6S comprising 30-74% or 31-73% or 36-70% or 40-67% or 40-66% or 42-65% or 44-64% or 42-45% or 48-65% of NS2S6S disaccharide group, 5-40% or 5-32% or 5-26% or 5-23% or 5-7% or 8-16% or 18-23% or 6-39% or 6-32% or 6-26% or 6-21% of NS6S disaccharide group, 1-28% or 1-27% or 4-28% or 4-27% or 8-28% or 8-27% or 10-28% or 11-28% or 12-27% or 11-22% or 19-27% of NS2S disaccharide group; and 0.5-23% or 0.5-20% or 0.5-19% or 0.5-18% or 0.5-17% or 1-21% or 1-19% or 1-18% or 1-17% or 1-15% of NS disaccharide group. The remainder of the third intermediate NS2S6S may comprise, or consist of one or more of OS, 2S, 6-O-sulfated, NAc (6S) 2-O-sulfated, 6-O-sulfated, NAc (2S6S) disaccharide groups. The third intermediate preferably does not contain 3S disaccharide groups. This method may comprise: (a) converting an amount of the N-acetyl glucosamine residues in heparosan to produce the a intermediate NS comprising 78-99.5% or 78-99% or 81-97% or 83-95% or 84-94% or 85-93% or 84-87% or 85-86% or 87.5-94% or 90-93.5% or 90.5-93% or 90.3-91.3% or 92.2-93.2% of N-sulfated (NS) disaccharide group (the converted amount of the N-acetyl glucosamine residues may correspond to the amount of NS groups in the first intermediate); (b) treating the first intermediate NS with an enzyme, such as C5-epimerase (C5-epi) and 2-O-sulfotransferase (2OST), in the presence of a sulfate donor, such as 3'-phosphoadenosine-5'-phosphosulfate (PAPS), to produce a second intermediate NS2S comprising 44-80% or 45-79% or 50-78% or 50-77% or 55-78% or 55-76% or 58-77% or 59-76% or 60-75% or 58-62% or 59-61% or 65-77% of NS2S disaccharide groups and 12-40% or 13-39% or 15-34% or 15-29% or 16-29% or 16-26% or 17-25% or 16-18% or 19-26% of NS disaccharide groups; and (c) treating the second intermediate NS2S with an enzyme, such as 6-O-sulfotransferases 1 and 3 (6OST-1,3), in the presence of a sulfate donor, such as phosphoadenosyl phosphosulfate (PAPS), to produce the third intermediate NS2S6S.

In some embodiments, the method may be a method of making a third intermediate NS2S6S comprising 41.5-45.5% or 42-45% or 42.5-44.5% or 43-44% of NS2S6S disaccharide group, 8.5-12.5% or 9-12% or 9.5-11.5% 10-11% of NS6S disaccharide group, 12-15% or 12.5-14.5% or 13-14% of NS2S disaccharide group and 14.6-18.6% or 15.1-18.1% or 15.6-17.6% or 16.1-17.1% of NS disaccharide group. The remainder of the third intermediate NS2S6S may comprise, or consist of one or more of OS, 2S, 6-O-sulfated, NAc (6S) 2-O-sulfated, 6-O-sulfated, NAc (2S6S) disaccharide groups. The third intermediate preferably does not contain 3S disaccharide groups. This method may comprise: (a) converting an amount of the N-acetyl glucosamine residues in heparosan to produce a first intermediate NS comprising 83.4-87.4% or 83.9-86.9% or 84.4-86.4% or 84.9-85.9% of N-sulfated (NS) disaccharide group (the converted amount of the N-acetyl glucosamine residues may correspond to the amount of NS groups in the first intermediate); (b) treating the first intermediate NS with an enzyme, such as C5-epimerase (C5-epi) and 2-O-sulfotransferase (2OST) in the presence of a sulfate donor, such as 3'-phosphoadenosine-5'-phosphosulfate (PAPS), to produce a second intermediate NS2S comprising 57.5-62.5% or 58-62% or 58.5-61.5% or 59-61% or 59.5-60.5% of NS2S disaccharide groups and 23.2-27.2% or 23.7-26.7% or 24.2-26.2% or 24.7-25.7% of NS disaccharide groups; and (c) treating the second intermediate NS2S with an enzyme, such as 6-O-sulfotransferases 1 and 3 (6OST-1,3), in the presence of a sulfate donor, such as phosphoadenosyl phosphosulfate (PAPS), to produce the third intermediate NS2S6S.

In some embodiments, the method may be a method of making a third intermediate NS2S6S comprising 51.3-60.3% or 51.8-59.8% or 52.3-59.3% or 52.8-58.8% of NS2S6S disaccharide group, 8.6-13.5% or 9.1-13% or 9.6-12.5% or 10.1-12% of NS6S disaccharide group, 10-15.8% or 10.5-15.3% or 11-14.8% or 11.5-14.3% of NS2S disaccharide group and 7.4-15.2% or 7.9-14.7% or 8.4-14.2% or 8.9-13.7% or 8.9-9.9% or 11.7-13.7% of NS disaccharide group. The remainder of the third intermediate NS2S6S may comprise, or consist of one or more of OS, 2S, 6-O-sulfated, NAc (6S) 2-O-sulfated, 6-O-sulfated, NAc (2S6S) disaccharide groups. The third intermediate preferably does not contain 3S disaccharide groups. This method may comprise: (a) converting an amount of the N-acetyl glucosamine residues in heparosan to produce the first intermediate NS comprising 88.8-94.7% or 89.3%-94.2% or 89.8-93.7% or 90.3%-93.2% of N-sulfated (NS) disaccharide group (the converted amount of the N-acetyl glucosamine residues may correspond to the amount of NS groups in the first intermediate); (b) treating the first intermediate NS with an enzyme, such as C5-epimerase (C5-epi) and 2-O-sulfotransferase (2OST) in the presence of a sulfate donor, such as 3'-phosphoadenosine-5'-phosphosulfate (PAPS), to produce a second intermediate NS2S comprising 65.8-74.4% or 66.3-73.9% or 66.8-73.4% or 67.3-72.9% of NS2S disaccharide groups and 17.9-26% or 18.4-25.5% or 18.9-25% or 19.4-24.5% of NS disaccharide groups; and (c) treating the second intermediate NS2S with an enzyme, such as 6-O-sulfotransferases 1 and 3 (6OST-1,3), in the presence of a sulfate donor, such as phosphoadenosyl phosphosulfate (PAPS), to produce the third intermediate NS2S6S.

In some embodiments, the method may be a method of making a third intermediate NS2S6S comprising 41.5-65.7% or 42-65.2% or 42.5%-64.7% or 43-64.2% of NS2S6S disaccharide group, 4.1-23.3% or 4.6-22.8% or 5.1%-22.3% or 5.6-21.8% of NS6S disaccharide group, 10-28.6% 10.5-28.1% or 11-27.6% or 11.5-27.1% or 11.1-17.8% or 19-27.6% of NS2S disaccharide group and 0.4-15.9% or 0.7-15.4% or 1-14.9% or 1-14.4% or 0.4-5.5% or 10.2-14.9% of NS disaccharide group. The remainder of the third intermediate NS2S6S may comprise, or consist of one or more of OS, 2S, 6-O-sulfated, NAc (6S) 2-O-sulfated, 6-O-sulfated, NAc (2S6S) disaccharide groups. The third intermediate preferably does not contain 3S disaccharide groups.

This method may comprise: (a) converting an amount of the N-acetyl glucosamine residues in heparosan to produce the first intermediate NS comprising 90.1-94.7% or 90.6-94.2% or 91.1%-93.7% or 91.6%-93.2% of N-sulfated (NS) disaccharide group (the converted amount of the N-acetyl glucosamine residues may correspond to the amount of NS groups in the first intermediate); (b) treating the first intermediate NS with an enzyme, such as C5-epimerase (C5-epi) and 2-O-sulfotransferase (2OST), in the presence of a sulfate donor, 3'-phosphoadenosine-5'-phosphosulfate (PAPS), to produce a second intermediate NS2S comprising 65.8-77.4% or 66.3-76.9% or 66.8-76.4% or 67.3-75.9% of NS2S disaccharide groups and 14.8-26% or 15.3-25.5% or 15.8-25% or 16.3-24.5% of NS disaccharide groups; and (c) treating the second intermediate NS2S with 6-O-sulfotransferases 1 and 3 (6OST-1,3) in the presence of phosphoadenosyl phosphosulfate (PAPS) to produce the third intermediate NS2S6S.

Another embodiment may be a method of making heparin, which may be bioequivalent to UPS heparin, comprising treating the third intermediate NS2S6S as disclosed above with an enzyme, such as 3-O-sulfotransferase isoform 1 (3OST-1), in presence of a sulfate donor, such as PAPS, to convert the 3-hydroxyl groups of the glucosamine residues to 3-O-sulfoglucosamine residues thereby producing heparin, which may be bioequivalent to porcine UPS Heparin Sodium.

In the aforementioned sulfotransferase reactions with 2OST, 3OST-1, one or both of 6OST-1 or 6OST-3, the enzymes may require a sulfate donor, which is typically PAPS, and a regeneration system. One or more enzymes, such as 2OST, 3OST-1, one or both of 6OST-1 or 6OST-3, and a sulfate donor, such as PAPS, may be in solution. The enzymes may be immobilized. In some embodiments, the reactions are performed in vitro. In other embodiments one or more steps occur inside a microbial host encoding genes for one or more of NDST, C5-Epi, 2OST, 3OST-1, one of 6OST-1 or 6OST-3, and a source of PAPS.

Although the disclosed above methods may produce heparin, which is bioequivalent to porcine USP heparin, in some embodiments, the produced heparin may be such that it does not satisfy one or more requirements of bioequivalency with porcine USP Heparin.

In some embodiments, the produced heparin batch may satisfy the requirements for porcine USP Heparin for molecular weight and anticoagulant activities, while not satisfying the requirements for porcine USP Heparin for anti-IIa activities. For example, the produced heparin batch may satisfy the requirements for porcine USP Heparin for molecular weight and anticoagulant activities, while having a ratio of activity on factor Xa to factor IIa (i.e. anti-Xa/anti-IIa) below 0.9, such as a value in 0.5-0.9 or 0.6-0.9 or 0.7-0.9 ranges, or above 1.1, such as a value in 1.1-1.5 or 1.1-1.4 or 1.1-1.3 or 1.1-1.2 ranges. Such batch may be converted into a heparin batch, which may be bioequivalent to porcine USP Heparin, with an additional enzyme treatment, such as treatment with 3-O-sulfotransferase isoform 1 (3OST-1), which may be performed in the presence of a sulfate donor, such as PAPS.

In some embodiments, the produced heparin batch may satisfy the requirements for porcine USP Heparin for anticoagulant activities, while not satisfying the requirements for porcine USP Heparin for anti-IIa activities and molecular weight. For example, the produced batch may have a ratio of activity on factor Xa to factor IIa (i.e. anti-Xa/anti-IIa) below 0.9, such as a value in 0.5-0.9 or 0.6-0.9 or 0.7-0.9, or above 1.1, such as a value in 1.1-1.5 or 1.1-1.4 or 1.1-1.3 or 1.1-1.2 ranges and using an additional enzyme treatment, such as treatment with 3-O-sulfotransferase isoform 1 (3OST-1), which may be performed in the presence of a sulfate donor, such as PAPS, to provide a ratio of activity on factor Xa to factor IIa, which satisfies the porcine USP Heparin requirements for anti-IIa activities.

Although the produced heparin may be bioequivalent to porcine USP heparin, in some embodiments, the produced heparin may be physically different for naturally produced heparin, such as bovine or porcine heparin, which still being bioequivalent to porcine USP heparin. For example, the present methods may allow producing batches of heparin, which may be bioequivalent to porcine USP heparin, such that the produced batches are more consistent or uniform among themselves in one or more of a) chemical composition, b) molecular weight, such as weight average molecular weight, and c) molecular weight distribution compared to naturally produced heparin batches, such as heparin batches from bovine intestine.

The present methods may producing heparin batches of at least 50 mg or at least 80 mg or at least 100 mg or at least 200 mg or at least 1 g or at least 2 g.

The produced batches may be consistent among themselves in molecular weight, disaccharide composition and biological activity. The produced batches of the above identified scale may all satisfy requirements for porcine USP heparin, such as molecular weight, disaccharide composition and biological activity requirements. The quantity of consistent batches may be at least 2 or at least 3 or at least 5 or at least 7 or at least 10 or at least 12 or at least 15 or at least 20.

The present disclosure also provides a pharmaceutical composition comprising a bioequivalent heparin produced using the disclosed above methods. The pharmaceutical composition may also include one or more pharmaceutically acceptable carriers or excepients. In some embodiments, the heparin may be, for example, formulated in water or in isotonic saline or glucose. In some embodiments, the heparin composition may include one or more preservatives, such as bisulfite or an antimicrobial, such as benzyl alcohol.

In some embodiments, the bioequivalent heparin produced according to this disclosure may be used in a form of a pharmaceutically acceptable salt, which may be, for example, sodium salt or potassium salt. Non-limiting examples of pharmaceutically acceptable salts include lithium, sodium, calcium, barium, potassium, magnesium, and ammonium.

In some embodiments, the bioequivalent heparin produced according to this disclosure above may be used as a starting material for the preparation of a low molecular weight heparin. This may be done, for example, by simply replacing porcine intestinal heparin with bioequivalent heparin produced according to this disclosure and then using one of known methods for the synthesis of a low molecular weight heparin. In one embodiment, a salt, such as for example, a sodium salt or a potassium salt, of bioequivalent heparin produced according to the present disclosure may be converted to the benzthonium salt that may then be benzylated and treated with a base, such as sodium hydroxide or potassium hydroxide, to partially depolymerize. The resulting low molecular weight heparin product would be converted to a salt, such as a sodium salt or a potassium salt, and purified. This process may afford a low molecular weight heparin, enoxaparin. Other processes may be used to convert bioequivalent heparin produced according to the present disclosure to other low molecular weight heparins, such as, for example, daltaparin or tinzaparin.

The present disclosure also includes a method of thinning blood in a subject, such as a human being, comprising producing bioequivalent heparin using one of the methods disclosed above and administering an effective amount of the produced bioequivalent heparin to the subject.

The present disclosure also includes a method of treating and/or preventing a disease or condition, which is susceptible to heparin, comprising producing bioequivalent heparin using one of the methods disclosed above and administering an effective amount of the produced bioequivalent heparin to a subject, such as a human being. Non-limiting examples of such disease or condition include deep vein, thrombosis, pulmonary embolism and arterial thromboembolism.

Bioequivalent heparin may also be used in extracorporeal therapy including kidney dialysis for patients with kidney failure or in blood oxygenation for patients undergoing cardiopulmonary bypass in open-heart surgery.

The effective amount of the bioequivalent heparin may mean an amount, which may be sufficient to produce a desired effect, such as thin blood or treat a disease or condition, which is susceptible to heparin.

Doses of bioequivalent heparin may be the same as doses used for USP heparin, which is produced naturally, such as porcine or bovine heparin.

The bioequivalent heparin may be administered using a number of administering modes. In some embodiments, the bioequivalent heparin may be administered parenterally. For example, the bioequivalent heparin may be injected intravenously, subcutaneously or intramuscularly.

The present disclosure also provides a composition comprising the first intermediate NS as disclosed above. Such composition may comprise at least 50% or at least 60% or at least 70% or at least 80% or at least at least 90% or at least 95% or at least 96% or at least 97% or at least 98% or at least 99% or at least 99.5% of the first intermediate NS. The composition may be such it is free or substantially free of any polysaccharide other than the first intermediate NS. The term "substantially free" may mean that any other polysaccharide cannot be detected in measurable amounts. Methods for detection may include nuclear magnetic resonance (NMR) spectroscopy or treatment with three heparin lyases breaking down heparin or heparin intermediate to disaccharides that can be removed through dialysis or size exclusion chromatography. Other non-heparin or non-heparin intermediates would be resistant to heparin lyase treatment and could be recovered and detected using conventional methods, such as NMR spectroscopy.

The present disclosure also provides a composition comprising the second intermediate NS2S as disclosed above. Such composition may comprise at least 50% or at least 60% or at least 70% or at least 80% or at least at least 90% or at least 95% or at least 96% or at least 97% or at least 98% or at least 99% or at least 99.5% of the second intermediate NS2S. The kit or composition may be such it is free or substantially free of any polysaccharide other than the second intermediate NS2S.

The present disclosure also provides a composition comprising the third intermediate NS2S6S as disclosed above. Such kit or composition may comprise at least 50% or at least 60% or at least 70% or at least 80% or at least at least 90% or at least 95% or at least 96% or at least 97% or at least 98% or at least 99% or at least 99.5% of the third intermediate NS2S6S. The kit or composition may be such it is free or substantially free of any polysaccharide other than the third intermediate NS2S6S. For example, in some embodiments, the kit or composition may be free or substantially free of heparin.

Embodiments described herein are further illustrated by, though in no way limited to, the following working examples.

EXAMPLES

Example 1

Production of heparosan.

*Escherichia coli* K5 (Serovar O10:K5:H4; ATCC #23506) or *Escherichia coli* Nissle 1917 (Serovar 06:K5:H1) was used for heparosan production (Cress, B. F., Toparlak, O. D., Guleria, S., Lebovich, M., Stieglitz, J. T., Englaender, J. A., Jones, J. A., Linhardt, R. J., and Koffas, M. A. G. (2015) CRISPathBrick: Modular Combinatorial Assembly of Type II-A CRISPR Arrays for dCas9-Mediated Multiplex Transcriptional Repression in *E. coli*. ACS Synthetic Biology. 4, 987-1000; Wang, Z., Ly, M., Zhang, F., Zhong, W., Suen, A., Hickey, A. M., Dordick, J. S., and Linhardt, R. J. (2010) *E. coli* K5 fermentation and the preparation of heparosan, a bioengineered heparin precursor. Biotechnology and Bioengineering. 107, 964-973; Wang, Z., Dordick, J. S., and Linhardt, R. J. (2011) *Escherichia coli* K5 heparosan fermentation and improvement by genetic engineering. Bioengineered bugs. 2, 63-67). High cell-density fed batch fermentations were performed at 5 L or 45-90 L using an Eppendorf BioFlo 320 or a Biostat fermenter, respectively. Cells were grown in a glucose defined media (pH 6.8±0.01), containing glucose (typically 20 g/L), potassium phosphate monobasic (typically 13.5 g/L), ammonium phosphate (typically 4.0 g/L), magnesium sulfate heptahydrate (typically 1.4 g/L), citric acid (typically 1.7 g/L), and trace metals solution (typically 10.0 ml/L) Trace metals solution in 5 M HCl (1.5 L) was composed of $FeSO_4.7H_2O$ (15 g), $CaCl_2$ (3.0 g), $ZnSO_4.7H_2O$ (3.3 g), $MnSO_4.H_2O$ (568 mg), $CuSO_4.5H_2O$ (1.5 g), $(NH_4)_6MO_7O_{24}.4H_2O$ (0.15 g), and $Na_2B_4O_7.10H_2O$ (0.03 g). Seed flasks (seed I), containing glucose defined media (pH 6.8±0.01) were inoculated with glycerol stocks and incubated for 8-16 h at 37° C. on a rotary shaker at 200-250 RPM. Next, seed flasks (seed II), containing glucose defined media (pH 6.8±0.01) were inoculated at 10% seeding density from seed I and incubated for 8-16 h at 37° C. on a rotary shaker at 200-250 RPM. Next, cells from seed II were inoculated at 5-10% seeding density in a fermenter containing sterilized glucose defined media (pH 6.8±0.01). Cells were grown at 30% dissolved oxygen, 37° C. and the pH was maintained at 6.8±0.01 using 2N HCl/5M $NH_4OH$. Dissolved oxygen levels, pH and cell growth (measured with optical density, $OD_{600nm}$) were monitored throughout the fermentation. The cells were fed exponentially and the feeding rate was controlled to maintain glucose concentration and dissolved oxygen level in the culture, with a concentrated sterilized feed containing glucose (700 g/L), supplemented with potassium phosphate monobasic (47 g/L) magnesium sulfate heptahydrate (20 g/L), thiamine (0.4 g/L) and trace metals solution (20 ml/L). Fermentations were stopped when $OD_{600}$ reached 135-200 (typically 140). Supernatant (containing heparosan) was harvested at 4° C. by centrifugation. The purification process of heparosan from culture supernatant included bleaching with sodium hypochlorite with 1.2 (%, w/w) and ammonium sulfate precipitation typically at 60% saturation. The precipitate was dissolved in water and dialyzed to obtain heparosan (Bhaskar, U. Chemoenzymatic Synthesis of Heparin for a Safer Bioengineered Alternative. PhD dissertation, Rensselaer Polytechnic Institute, Troy, N.Y., USA (2014)).

Example 2

Production of intermediate #1 (NS).

Heparosan obtained from example 1 was chemically N-deacetylated and depolymerized as previously reported (Z. Wang, J. Li, S. Cheong, U. Bhaskar, A. Onishi, F. Zhang, J. S. Dordick, R. J. Linhardt (2011), Response surface optimization of the heparosan N-deacetylation in producing bioengineered heparin, Journal of Biotechnology, 156, 188-196). A 1% concentration of heparosan was reacted with 1M sodium hydroxide at 50 to 55° C. for 18 to 28 h. Then, the reaction mixture was adjusted to pH 7 with HC1, followed by 48 h of chemical N-sulfonation by excess amount of sulfur trioxide trimethylamine complex. Then, ethanol precipitation was used to fractionate the first intermediate NS with desired molecular weight properties (A. Onishi (2015), Detailed physicochemical and biological analyses of heparins from various sources, PhD dissertation, Rensselaer Polytechnic Institute, Troy, N.Y., USA). The NS disaccharide group content of the first intermediate NS was 78.3 to 99.3 mol %. Molecular weight was 15,100 to 18,100 Da, the percentage of heparin polysaccharides chains with molecular weight of greater than 24,000 was 7,0 to 17.4; the percentage of chains with molecular weights ranging from 16,000 to 24,000 Da was 1.1 to 2.3.

Example 3

Disaccharide analysis, and molecular weight analysis, and activity analysis.

Disaccharide Analysis Overall

Disaccharide analysis was used to measure the disaccharide composition of porcine USP heparin or bioengineered heparin intermediates. A sample is digested into eight constituent disaccharides by treatment with heparinase I, II and III. The disaccharides generated are then separated and measured by high-pressure liquid chromatography-ultraviolet (HPLC-UV) spectrometry. For NS (first intermediate), $^1$H-nuclear magnetic resonance (NMR) spectroscopy can also be used to quantify the two constitutional disaccharides (i.e., OS and NS). While the disaccharide compositions of the invention are described as mole %, it is well known in the art that they can also be described as area under the curve (AUC) %, as weight %, or by other known terminology within the scope of invention.

It should be noted that in the invention, disaccharide AUC % is equal to disaccharide mol % with an assumption that all eight disaccharides have the same molar extinction coefficient at 232 nm, which is believed to be an appropriate assumption for several reasons. First, it is well known that each of the eight disaccharides has exactly one Δ-4-5 unsaturated uronic acid (ΔUA) in the structure. Second, a recent paper on heparin disaccharide analysis indicated that disaccharide quantification is based on the data driven consensus assumption that molar extinction coefficient at 232 nm for Δ-4-5 unsaturated oligosaccharides are "constant" (P. Mourier et al. Quantitative compositional analysis of heparin using exhaustive heparinase digestion and strong anion exchange chromatography. Anal. Chem. Res. 3, 46-53 (2015)) Third, there is consistency of molar extinction coefficient at 232 nm among five different heparin derived oligosaccharides (5063+/−10%, 5331+/−0.6%, 5066+/−3.7%, 5657+/−1.4% and 5275+/−%, $M^{-1}cm^{-1}$) (K. G. Rice and R. J. Linhardt. Study of structurally defined oligosaccharide substrates of heparin and heparan monosulfate lyases. Carbohydr. Res. 190, 219-233 (1989)). Lastly, an almost identical assumption is actually used in the current porcine USP heparin; an analytical method in the porcine USP heparin assumes that all of such eight disaccharides have the same molar extinction coefficient at the very close 234 nm wavelength (USP40 Chemical Tests, <207>Test for 1,6-Anhydro Derivative for Enoxaparin Sodium, pp 261-266. (United States Pharmacopoeial Convention, Rockville, Md., USA, 2017)). In $^1$H-NMR, relative AU % is equivalent to mol %.

Intermediates Analysis by 1H-NMR

ID $^1$H-NMR was conducted at the following conditions: temperature 298 K, recycle delay time at least 2-s, acquisition time at least 0.75 s, number of scans at least 16, solvent was D2O. ID $^1$H-NMR spectra of purified heparosan, each intermediate, biosynthetic heparin and USP porcine heparin were shown as FIG. 3. With four steps of chemoenzymatic modifications from precursor heparosan to final product, the resulted biosynthetic heparin had highly similar chemical structure compared with USP porcine heparin.

Regarding the disaccharide analysis of the First intermediate by 1H-NMR, the peak area of H-1 proton of a glucosamine residue was used for quantification. The H-1 proton of N-acetyl glucosamine (OS disaccharide) appeared at around 5.31 ppm while the H-1 proton of N-sulfo glucosamine (NS disaccharide) appeared at around 5.55 ppm. The disaccharide composition is expressed as mol %; AUC % is equivalent to mol %.

Disaccharide Analysis by HPLC-UV

Briefly, an analytical sample is digested by heparinases, and then the generated disaccharides are separated and measured by strong anion exchange (SAX)-HPLC-UV.

The typical analytical conditions are as follows; it should be noted that non-essential minor modification(s) that does not affect disaccharide compositions, such as a linear scale-down/scale-up of the heparinases digestion reaction, temperature change of the SAX column up to 50° C., may be applied.

An analytical sample (100 μg) was mixed with the concentrated digestion buffer (final concentration is 50 mM NH$_4$OAc, 2 mM CaCl$_2$), heparinase I, II, and III from *Flavobacterium heparinum* (>100 mIU of each heparinase, prepared by our laboratory as described in (Zhang, F., et al. Structural characterization of heparins from different commercial sources. Anal. Bioanal. Chem. 401, 2793-2803 (2011)., Zhang Z, X. J., Liu H, Liu J, Linhardt R J. Quantification of Heparan Sulfate Disaccharides Using Ion-Pairing Reversed-Phase Microflow High-Performance Liquid Chromatography with Electrospray Ionization Trap Mass Spectrometry. Anal. Chem. 81, 4349-4355 (2009)), and water so that the total volume was 200 μL. The mixture was incubated at 35° C. for 2 h. After the incubation, the generated disaccharides were separated from heparinases by using either (a) ultrafiltration with 3 kDa molecular weight-cutoff spin column (Amicon Ultra-0.5 Centrifugal Filter Unit with Ultracel-3 membrane, EMD Millipore, Billerica, MA, USA), or, (b) incubation at 95° C. for at least 5 min followed by centrifuge. Direct comparison study by using Second intermediate NS2S, Third intermediate NS2S6S and USP heparin, showed that the difference between (a) and (b) were at most 2.6 w/w %. 20 μL of the generated disaccharide was injected onto a SAX chromatography column (Spherisorb-SAX chromatography column, 4.0×250 mm, 5 μm, Waters, France). Column temperature was 40° C. The mobile phase A was 1.8 mM NaH2PO4 adjusted to pH 3.0 with phophoric acid and the mobile phase B was 1.8 mM NaH2PO4 adjusted to pH 3.0 with 1 M NaClO4. A linear gradient of the mobile phase B (0 min, 3% B; 20 min, 35% B; 50 min, 100% B; 60 min, 3% B, 80 min, 3% B) was applied with a flow rate of 0.45 mL/min. UV detection was performed at 232 nm because unsaturated uronic acid (ΔUA) of each disaccharide has UV absorbance at this wavelength. Disaccharide standards were purchased from Iduron (Manchester, UK) to identify the peaks belonging to each disaccharide at 232 nm. To ensure the accuracy and precision of the analysis, commerical Heparin Sodium active pharmaceutical ingredient (Celsus, Cincinnati, Ohio, USA) was also digested and analyzed in each analysis. To ensure the linearity of HPLC peak area, a series of dilutions of disaccharide standards were analyzed in each analysis. Disaccharide composition was expressed either w/w % and/or mol %. The w/w % values were calculated based on the standard curves by a series of commercial standards. The mol % values were calculated by the following formula:

Dissacharide $i$ mol %=(100×A$i$)/(ΣxAx), where Ai is the peak area at 232 nm of the disaccharide i. Ax is the peak area; the sum being related to all the eight disaccharides that appeared in the Definitions of the specification. Again, in the invention, AUC % of disaccharide is equal to mol % of disaccharide with an assumption that all of the 8 disaccharides have the same molar extinction coefficient at 232 nm.

Disaccharide Analysis by HPLC-MS

The analysis was performed as described in a paper (Bhaskar, U. *Chemoenzymatic Synthesis of Heparin for a Safer Bioengineered Alternative*. PhD dissertation, Rensselaer Polytechnic Institute, Troy, N.Y. (2014).

In detail, 10 µg of analytical sample in 25 µL of water was mixed with heparinase I, II, and III from *Flavobacterium heparinum* (>10 mIU of each heparinase) in 5 µL of concentrated buffer (25 mM Tris, 500 mM NaCl, 300 mM imidazole, pH 7.4). The mixture was incubated at 35° C. for 10 h. After the incubation, the generated disaccharides were recovered by centrifugal filtration with 10 kDa molecular weight-cutoff spin column (YM-10 micro-concentrator, EMD Millipore, Billerica, Mass., USA). The flow-through was dissolved in water to a concentration of 50-100 ng/2 µL for liquid chromatography (LC)-mass spectrometric (MS) analysis.

LC-MS analysis was performed on an Agilent 1200 LC/MSD instrument (Agilent Technologies, Inc. Wilmington, Del., USA) equipped with a 6300 ion trap and a binary pump followed by a UV detector. The column used was a Poroshell 120 C18 column (2.1×100 mm, 2.7 µm, Agilent, USA). Eluent A was water/acetonitrile (85:15) v/v, and eluent B was water/acetonitrile (35:65) v/v. Both eluents contained 12 mM tributylamine and 38 mM ammonium acetate with pH adjusted to 6.5 with acetic acid. A gradient of solution A for 5 min followed by a linear gradient from 5 to 15 min (0-40% solution B) was used at flow rate of 150 µL/min.

Molecular Weight and Concentration Determinations

Molecular weights were determined via gel permeation chromatography (GPC), in accordance with the USP 37 Heparin monograph method, with non-essential minor modifications. A guard column TSK SWXL 6-mm×4-cm, 7-µm diameter was used in series with two analytical columns: TSK G4000 SWXL 7.8-mm×30 cm, 8-µm in series with TSK G3000 SWXL 7.8-mm×30-cm, 5-µm (Tosoh Corporation, Minato-Ku, Tokyo, Japan). These columns were connected to an HPLC system consisting of Shimadzu LC-20AD pump, a Shimadzu CBM-20A controller, Shimadzu SIL-20AHT auto-sampler, Shimadzu CTO-20AC column oven, and a Shimadzu RID-20A refractive index detector (Shimadzu, Kyoto, Japan). Columns and RID detector were maintained at 30° C. The mobile phase was 0.1 M ammonium acetate with 0.02 wt % sodium azide and the flow rate was 0.6 mL/min. A sample injection volume was 20 µL. The GPC chromatograms were recorded with the LC solution version 5.73 software (Shimadzu, Kyoto, Japan), and analyzed with its "GPC Postrun" function. For molecular weight determination, USP Heparin Sodium Molecular Weight Calibrant RS (reference standard) was used as a calibrant and USP Heparin Sodium Identification RS (USP, MD, US) was used to confirm system suitability. Also, USP Heparin Sodium Identification RS prepared as several concentrations were injected to get a standard curve to calculate the concentration of reaction samples using area under the curve (AUC). All data passed System Suitability requirements as stated in the USP monograph. For calculation, a third order polynominal equation was used. The definitions of molecular weight parameters are below.

The weight-average molecular weight (MW) is calculated with $$M_W = \frac{\sum_i N_i M_i^2}{\sum_i N_i M_i},$$

where Ni is the number of molecules of molecular weight Mi. M24000 is a percentage of heparin chains with molecular weight greater than 24,000 Da. M8000-16000/M16000-24000 is a ratio of the percentage of heparin with molecular weight in the range 8,000-16,000 Da, to the percentage of heparin with molecular weight in the range 16,000-24,000 Da.

In Vitro Anticoagulant Activity Measurement

The anti-Xa and anti-IIa activities of heparins were determined using BIOPHEN Heparin Anti-Xa (two stage) and Anti-IIa (two stage) kits (Aniara, West Chester, Ohio). Human ATIII 40 mU in 80 µL R1 buffer (Tris 0.05 M, NaCl 0.175 M, EDTA 0.0075 M, at pH 8.40 containing polyethylene glycol at 0.1 wt %, and 0.02 wt % sodium azide as preservative) was used for anti-Xa assay. Human ATIII 10 mU in 80 µL R2 buffer (Tris 0.05 M, NaCl 0.175 M, EDTA 0.0075 M, at pH 8.40 containing bovine serum albumin at 0.2 wt %, and 0.02 wt % sodium azide as preservative) mixed with different masses of heparin (range from 0, 5, 10, 15, and 20 ng) were incubated for 2 min at 37° C. Then, purified bovine factor Xa (320 ng in 40 µL R1 buffer) or purified human thrombin (960 mU in 40 µL in R2 buffer) preincubated at 37° C. were added and incubated for 2 min before the addition of chromogenic substrate specific for factor Xa (CS-01(65), 1.2 mM, 40 µL) or the chromogenic substrate specific for thrombin (CS-01(38), 1.25 mM, 40 µL). The reaction mixture was incubated at 37° C. for 2 min for anti-Xa assay and 1 min for anti-IIa assay and then stopped with citric acid (20 mg/mL, 80 µL). The absorbance was measured at 405 nm. Anti-Xa and anti-IIa activities were calculated using a standard curve of different concentrations of heparin (0-1 U/mL).

Example 4: Production of enzymes (C5-epimerase, 2OST, 6OST-1, 6OST-3, 3OST-1, AST-IV).

The cell pellet (10 g wet weight) of MBP-tagged enzymes (C5 epi, 2OST, 6OST-1, and 6OST-3) was dispersed in 50 mL of purification buffer (25 mM Tris-HCl (BioRad, USA), 500 mM NaCl (Sigma, USA), pH 7.5) containing protease inhibitor (Sigma, USA) and 8000 kU/L DNAse I (Sigma, USA). The resultant cell suspension was passed through microfuidizer (Microfluidics LM20, USA) at 15000 psi for cell lysis. The cell debris was removed by centrifugation at 13000 g for 30 min at 4° C. The soluble enzyme was purified using 10 mL of amylose resin (NEB, USA) according to manufacturer's instructions.

The cell pellet (10 g wet weight) of His6-tagged enzymes (3OST-1 and AST-IV) was dispersed in 50 mL of purification buffer (25 mM Tris-HCl, 500 mM NaCl, 30 mM Imidazole, pH 7.5) containing protease inhibitor and 8000 kU/L DNAse I. The cell lysis was performed as described before and the soluble enzyme was purified using 10 mL of Ni-NTA sepharose (GE Healthcare, Sweden) according to manufacturer's protocol. Purified enzymes were analyzed by SDS-PAGE gel (BioRad, USA) analysis.

Example 5

Preparation and activity characterization of immobilized enzyme catalysts.

The His6-tagged enzymes (3OST-1 and AST-IV) were eluted with 25 mM Tris-HCl (pH 7.5) buffer containing 500 mM NaCl and 500 mM imidazole from Ni-NTA sepharose beads and the MBP-tagged enzymes (C5 epi, 2OST, 6OST-1, and 6OST-3) were eluted from amylose resin with 25 mM Tris-HCl (pH 7.5) buffer containing 500 mM NaCl and 40 mM maltose. The buffer of eluted enzymes was replaced with coupling buffer (sodium phosphate buffer (Alfa Aesar, USA), 100 mM; NaCl, 150 mM; pH 7.5) using 10 kDa centrifugal filter (Millipore, USA). For covalent immobilization of enzymes, 30-40 mg of commercial beads, e.g., CNBr Sepharose (GE Healthcare, Sweden), Azlactone based Ultralink Biosupport (ThermoFisher, USA) and NHS-agarose (Thermo Fisher, USA) were incubated with 1-2 mg of enzymes individually for 1 h at room temperature with gentle flipping (as per manufacturer instructions). After covalent immobilization, the respective beads were washed with coupling buffer and left over functional groups on beads were quenched using quenching buffer (100 mM Tris-HCl and 1 M NaCl at pH 8.0) (as per manufacturer instructions). The coupling efficiency of enzymes on the respective beads was calculated by measuring initially added enzyme and unbound enzyme in the supernatant, washes and quenching solution. The amount of enzyme was calculated using SDS-Page gel analysis by ImageLab software (Bio-Rad, USA) and BCA (Thermo Fisher, USA) assay. Bovine serum albumin (BSA) (ThermoFisher, USA) was used as standard for coupling efficiency calculations.

Example 6

Production of intermediate #2 (NS2S).

This sulfation step can be performed with or without a PAPS recycling system comprising PNPS, PAPS and immobilized AST-IV. The first intermediate NS was treated with immobilized 2OST and C5-epi. The detailed enzymatic reaction conditions were as follows in MES reaction buffer (50 mM, pH 7.2): 1 mg/mL NS, 0.25 mg/mL C5 epi, 0.5 mg/mL 2OST, 10 mM p-nitrophenylsulfate (PNPS) and 1 mM PAP (only if recycling system was applied), reaction temperature at 37° C. and reaction time of 24 h. For non-recycle reactions, the same conditions as above were used except in the absence of PAP, PNPS and AST-IV, 1.2 mM excess of PAPS concentration was dependent on the target NS2S conversion rate. Fresh enzymes were prepared and immobilized before reaction as described in Examples 4 and 5. For purification, a 5 kDa MWCO membrane ultrafiltration was used to remove post-reaction compounds such as PAP and PAPS (plus PNP and PNPS if recycling was applied). The retentates were concentrated and collected for disaccharide analysis. This step could be repeated if the NS2S % did not reach the target.

Example 7: Production of intermediate #3 (NS2S6S and NS6S).

The reaction step for production of intermediate #3 follows the method used for intermediate #2 except NS2S replaces NS and immobilized 6OST-1 and 6OST-3 (both at 0.5 mg/mL) replace C5-epi and 2OST. This reaction could be repeated if the NS2S6S (TriS) % did not reach the target.

Example 8

Production of biosynthetic heparin.

Immobilized recombinant enzyme 3OST-1 was prepared by the same manner as mentioned in Example 5. The reactions were performed under the same conditions as used for the second and third intermediates except the enzymes were replaced with immobilized 3OST-1. The final biosynthetic heparin was purified using Strong Anion Exchange (SAX) chromatography with Q Sepharose resin. Briefly, biosynthetic heparin was bound to resin in 40 mM NaCl solution followed by a 400 mM NaCl solution wash. The purified biosynthetic heparin was eluted using 4 M NaCl solution followed by desalting and concentrating. The purified biosynthetic heparin was collected for further disaccharide compositional analysis, molecular weight analysis and in Vitro anticoagulant activity assays as indicated in Example 3. This step could be repeated if the anticoagulant activity did not reach USP specification.

Example 9

Precise methods for the synthesis of two biosynthetic heparins (BSH) with activity and molecular weight properties that meet specifications of porcine USP Heparin and two biosynthetic heparins (BSH) that do not meet activity and molecular weight specifications of porcine USP Heparin.

Production of biosynthetic heparin batch h

A total of 40 mg NS (85.4% NS content) was treated with 2OST and C5-epi under the conditions described in Example 6. The reaction conditions were as follows in MES reaction buffer (50 mM, pH 7.2): 1 mg/mL NS, 0.25 mg/mL C5 epi, 0.5 mg/mL 2OST, and 1.45 mM PAPS. The reaction was incubated on a roller at 37° C. for 24 h. Enzyme beads were removed from the solution and were washed with 3 column volumes (CV) 50 mM MES buffer (pH 7.2) to recover the polysaccharide. The reaction solution and 3 CV washing buffer were combined and loaded onto a 5 kDa MWCO membrane spin column for concentrating and removing the post-reaction compounds. The retentate was collected and sampled for disaccharide analysis as mentioned in Example 3. The disaccharide composition of resulted NS2S intermediate is as shown in Table 3.

TABLE 3

Summary of disaccharide composition history and anticoagulant activity for biosynthetic heparin batch h.

| Batch h | 0S | NS | 6S | 2S | NS6S | NS2S | 2S6S | TriS | Anti-Xa | Anti-IIa | Xa/IIa |
|---|---|---|---|---|---|---|---|---|---|---|---|
| First Intermediate NS | 14.6 | 85.4 | — | — | — | — | — | — | | — | |
| Second Intermediate NS2S | 13.8 | 25.2 | 0.0 | 1.0 | 0.0 | 60.0 | 0.0 | 0.0 | | | |
| Third Intermediate NS2S6S $1^{st}$ 6OSTs | 12.7 | 20.8 | 1.2 | 0.9 | 4.9 | 22.3 | 0.1 | 37.2 | | | |
| Third Intermediate NS2S6S $2^{nd}$ 6OSTs | 11.8 | 16.6 | 3.2 | 0.8 | 10.5 | 13.5 | 0.1 | 43.5 | | | |
| BSH batch h $1^{st}$ 3OST | 12.6 | 16.1 | 1.7 | 0.7 | 9.1 | 14.8 | 0.0 | 44.9 | — | 163 | — |
| BSH batch h $2^{nd}$ 3OST | 15.1 | 17.1 | 0.7 | 0.5 | 5.7 | 12.5 | 0.0 | 48.4 | 365 | 396 | 0.92 |

In the second enzymatic step, 3 mg of the resulting NS2S intermediate with 60% NS2S content was treated with immobilized 6OST-1 and 6OST-3 to generate the NS2S6S intermediate. The immobilization method was as mentioned in Example 5. Sulfation reaction conditions were the same as mentioned in Example 7. After reaction completion, polysaccharide was recovered, purified and analyzed as mentioned above for NS2S production. The disaccharide composition of this NS2S6S intermediate after $1^{st}$ 6OSTs treatment was as shown in Table 3. In order to increase TriS % up to more than 40%. 6OSTs treatment was repeated again using the same method. The resulted NS2S6S intermediate post-$2^{nd}$ treatment obtained NS2S6S disaccharide of 43.5% and NS6S disaccharide of 10.5%.

This NS2S6S intermediate after the $2^{nd}$ 6OSTs treatment (85.4-60.0-43.5) was further treated with immobilized 3OST-1 to generate biosynthetic heparin batch h. The 3OST-1 immobilization was performed as described in Example 5. Sulfation reaction conditions and purification methods of biosynthetic heparin batch h were the same as described in Example 8, and followed with molecular weight, disaccharide determination and in Vitro activity assays as mentioned in Example 3. Biosynthetic heparin batch h, after the $1^{st}$ 3OST-1 treatment, only reached anti-IIa activity of 160 U/mg which is lower than the porcine USP heparin 180 U/mg specification (Table 3). Thus, the intermediate was treated again with 3OST-1 followed by using the same purification and analysis as described above. Biosynthetic heparin batch h after the $2^{nd}$ 3OST-1 treatment had anti-IIa of 396 U/mg, anti-Xa of 365 U/mg and anti-Xa/anti-IIa of 0.92 with a weight average molecular weight of 17,500 Da, a percentage of fractions with Mw higher than 24,000 of 16.8, and the ratio between fractions with Mw of 8,000 to 16,000 and Mw of 16,000 to 24,000 each of 1.3. Both anticoagulant activity and molecular weight properties of biosynthetic heparin batch h were within porcine USP heparin specifications.

Production of biosynthetic heparin batch w

A total of 25 mg NS (92.7% NS content) was treated with 2OST and C5 epi under the conditions described in Example 6. Briefly, the reaction conditions were as follows: 1 mg/mL (2.23 mM) NS, 0.25 mg/mL C5-epi, 0.5 mg/mL 2OST, 0.5 mg/mL AST-IV, 10 mM PNPS and 1.61 mM PAPS in 50 mM MES buffer (pH 7.2). The reaction was incubated on a roller at 37° C. for 24 h. Enzyme beads were removed from the solution and were washed with 3 column volumes (CV) using 50 mM MES buffer (pH 7.2) to recover all polysaccharide. Reaction solution and 3 CV washing buffer were combined and loaded into a 5 kDa MWCO membrane spin column for concentrating and removing the post-reaction compounds. The retentate was collected and sampled for disaccharide analysis as mentioned in Example 3. The disaccharide composition of resulted NS2S intermediate is as shown in Table 4. This substrate after the $1^{st}$ 2OST/C5-epi treatment only reached NS2S % of 68.9%. Thus, the 2OST-1/C5 reaction was repeated twice to increase the NS2S % to 75% using the same method (Table 4).

A total of 3 mg of the resulting NS2S intermediate with 75.4% NS2S disaccharide group was further treated with immobilized 6OST-1 and 6OST-3 to generate the NS2S6S intermediate. The immobilization method was as mentioned in Example 5. Sulfation reaction conditions were the same as mentioned in Example 7 with the PAPS recycling system. After reaction completion, polysaccharide was recovered, purified and analyzed as mentioned above for the NS2S production step. The disaccharide composition of this NS2S6S intermediate after 6OST-1&3 treatment is shown in Table 4, and contained NS2S6S (TriS) disaccharide of 54.5% and NS6S disaccharide of 14.3%.

This NS2S6S intermediate was further treated with immobilized 3OST-1 to generate biosynthetic heparin batch w. The 3OST-1 immobilization was as mentioned in Example 5. Sulfation reaction conditions and purification methods of biosynthetic heparin batch w were the same as Example 8 with PAPS recycling, and followed with molecular weight, disaccharide determination and in vitro activity assays as mentioned in Example 3. Biosynthetic heparin batch w post-3OST-1 treatment reached anti-IIa activity of 343 U/mg, anti-Xa of 393 U/mg and anti-Xa/anti-IIa of 1.10, with a weight average molecular weight of 15,500 Da, the percentage of fractions with molecular weight higher than 24,000 of 6.6, and the ratio between fractions with Mw of 8,000 to 16,000 and Mw of 16,000 to 24,000 of 1.7. Both anticoagulant activity and Mw of biosynthetic heparin batch w were within porcine USP heparin specifications.

TABLE 4

Summary of disaccharide composition history and anticoagulant activity for biosynthetic heparin batch w.

| Batch w | 0S | NS | 6S | 2S | NS6S | NS2S | 2S6S | TriS | Anti-Xa | Anti-IIa | Xa/IIa |
|---|---|---|---|---|---|---|---|---|---|---|---|
| First Intermediate NSH | 7.3 | 92.7 | — | — | — | — | — | — | — | | |
| Second Intermediate NS2S 1$^{st}$ 2OST/C5 | 6.5 | 24.0 | 0.0 | 0.6 | 0.0 | 68.9 | 0.0 | 0.0 | | | |
| Second Intermediate NS2S 2$^{nd}$ 2OST/C5 | 6.5 | 17.9 | 0.0 | 1.0 | 0.0 | 74.5 | 0.0 | 0.0 | | | |
| Second Intermediate NS2S 3$^{rd}$ 2OST/C5 | 6.8 | 16.8 | 0.0 | 1.0 | 0.0 | 75.4 | 0.0 | 0.0 | | | |
| Third Intermediate NS2S6S | 1.5 | 2.5 | 4.9 | 0.4 | 14.3 | 21.4 | 0.6 | 54.5 | | | |
| BSH batch w | 1.5 | 2.7 | 1.8 | 0.4 | 9.3 | 23.5 | 0.3 | 60.5 | 393 | 343 | 1.10 |

In some instances of biosynthetic heparin batches, single enzymatic treatments for the second and third intermediates, respectively, meet porcine USP heparin specifications.

Production of biosynthetic heparin batch 1 that does not meet porcine USP Heparin activity and molecular weight specifications A total of 140 mg NS (92.7% NS content) was treated with 2OST-1 and C5-epi under the conditions mentioned in Example 6. Briefly, the reaction conditions were as follows: 1 mg/mL (2.23 mM) NS, 0.25 mg/mL C5 epi, 0.5 mg/mL 2OST, and 2 mM PAPS in 50 mM MES buffer (pH 7.2). The reaction was incubated on a roller at 37° C. for 24 h. Enzyme beads were removed from the solution and were washed with 3 column volumes (CV) using 50 mM MES buffer (pH 7.2) to recover all substrate. Reaction solution and 3 CV washing buffer were combined and loaded into a 5k Da MWCO membrane spin column for concentrating and removing the post-reaction compounds. The retentate was collected and sampled for disaccharide analysis as mentioned in Example 3. The second intermediate NS2S reached NS2S disaccharide of 72.4% according to disaccharide analysis (Table 5).

A total of 10 mg of the resulting NS2S intermediate with 72.4% NS2S disaccharide content was further treated with immobilized 6OST-1 and 6OST-3 to generate the NS2S6S intermediate. The immobilization method was as mentioned in Example 5. Sulfation reaction conditions were the same as mentioned in Example 7. After reaction completion, polysaccharide was recovered, purified and analyzed as mentioned above in the NS2S sulfation step. The disaccharide composition of this NS2S6S intermediate after 6OST-1&3 treatment is shown in Table 5 and consisted of NS2S6S (TriS) disaccharide of 41.0% and NS6S disaccharide of 3.7%.

This NS2S6S intermediate was further treated with immobilized 3OST-1. The 3OST-1 immobilization was as mentioned in Example 5. Sulfation reaction conditions and purification method were the same as Example 8, and followed with weight average molecular weight, disaccharide composition and in vitro activity assays as mentioned in Example 3. This batch post-3OST-1 treatment only reached anti-IIa activity of 112 U/mg, anti-Xa of 93 U/mg and anti-Xa/anti-IIa of 0.80. In order to increase anti-IIa activity to meet USP specification, this non-equivalent batch 1 was treated with immobilized 3OST-1 again using the same method as mentioned in Example 8. However, the anti-IIa activity still remained low (114 U/mg) not reaching the required 180 U/mg as per porcine USP heparin specifications.

TABLE 5

Summary of disaccharide composition history and anticoagulant activity for biosynthetic heparin batch 1.

| Batch 1 | 0S | NS | 6S | 2S | NS6S | NS2S | 2S6S | TriS | Anti-Xa | Anti-IIa | Xa/IIa |
|---|---|---|---|---|---|---|---|---|---|---|---|
| First Intermediate NSH | 7.3 | 92.7 | — | — | — | — | — | — | — | | |
| Second Intermediate NS2S | 6.5 | 20.4 | 0.0 | 0.7 | 0.0 | 72.4 | 0.0 | 0.0 | | | |
| Third Intermediate NS2S6S | 6.3 | 17.2 | 0.5 | 0.8 | 3.7 | 30.6 | 0.0 | 41.0 | | | |
| Non-BSH batch 1 (1$^{st}$ 3OST) | | | | | Not tested | | | | 93 | 112 | 0.80 |
| Non-BSH batch 1 (2$^{nd}$ 3OST) | 6.7 | 15.7 | 0.1 | 1.0 | 3.5 | 28.2 | 0.0 | 44.8 | 114 | 114 | 1.00 |

Production of biosynthetic heparin batch 2 that does not meet porcine USP Heparin activity and molecular weight specifications A total of 40 mg NS (92.7% NS content) was treated with 2OST and C5-epi under the condition mentioned in Example 6. Briefly, the reaction conditions were as follows: 1 mg/mL (2.23 mM) NS, 0.25 mg/mL C5 epi, 0.5 mg/mL 2OST, and 2 mM PAPS in 50 mM MES buffer (pH 7.2). The reaction was incubated on a roller at 37° C. for 24 h. Enzyme beads were removed from the solution and were washed with 3 column volumes (CV) using 50 mM MES buffer (pH 7.2) to recover all polysaccharide. Reaction solution and 3 CV washing buffer were combined and loaded into a 5 kDa MWCO membrane spin column for concentrating and removing the post-reaction compounds. The retentate was collected and sampled for disaccharide analysis as mentioned in Example 3. The second intermediate NS2S reached NS2S disaccharide of 81.4% according to disaccharide analysis (Table 6).

A total of 3 mg of the resulted NS2S intermediate with 81.4% NS2S disaccharide content was further treated with immobilized 6OST-1 and 6OST-3 to generate NS2S6S intermediate. The immobilization method was as mentioned in Example 5. Sulfation reaction conditions were the same as mentioned in Example 7. After reaction completion, polysaccharide was recovered, purified and analyzed as mentioned above in NS2S sulfation step. The disaccharide composition of this NS2S6S intermediate after 6OST-1&3 treatment is shown in Table 6 and consisted of NS2S6S (TriS) disaccharide of 61.0% and NS6S disaccharide of 2.5%.

This NS2S6S intermediate was further treated with immobilized 3OST-1. The 3OST-1 immobilization was as mentioned in Example 5. Sulfation reaction conditions and purification method were the same as Example 8, followed by weight average molecular weight, disaccharide content and in vitro activity assays as mentioned in Example 3. This batch post-3OST-1 treatment only reached anti-IIa activity of 49 U/mg, which was far away from USP specification of 180 U/mg. This non-equivalent batch 2 proved to be non-equivalent to porcine USP heparin.

TABLE 6

Summary of disaccharide composition history and anticoagulant activity for biosynthetic heparin batch 2.

| Batch 2 | 0S | NS | 6S | 2S | NS6S | NS2S | 2S6S | TriS | Anti-Xa | Anti-IIa | Xa/IIa |
|---|---|---|---|---|---|---|---|---|---|---|---|
| First Intermediate NSH | 7.3 | 92.7 | — | — | — | — | — | — | | | — |
| Second Intermediate NS2S | 5.2 | 11.2 | 0.0 | 2.2 | 0.0 | 81.4 | 0.0 | 0.0 | | | |
| Third Intermediate NS2S6S | 4.5 | 8.3 | 0.8 | 2.0 | 2.5 | 20.7 | 0.2 | 61.0 | | | |
| Non-BEqH batch 2 (2$^{nd}$ 3OST) | 4.3 | 7.6 | 0.5 | 1.8 | 2.0 | 22.5 | 0.0 | 61.3 | — | 49 | — |

GENERATION OF BIOSYNTHETIC HEPARIN THROUGH THREE INTERMEDIATES

Overview

Described below are multiple batches of biosynthetic heparin that met the USP requirements for biological activity and, when measured, for molecular weight. The biosynthetic heparin also exhibited a disaccharide content equivalent to porcine USP heparin. These experiments were done in tandem with high performance liquid chromatography and nuclear magnetic resonance spectroscopy to quantitatively ascertain the extent and nature of sulfation.

The generation of biosynthetic heparin requires that the intermediates generated at each step of the process consist of specific disaccharide contents. Described below is specific information on: (a) the NS disaccharide group content (all contents in terms of % of overall disaccharide composition) of the first intermediate NS; (b) the NS2S and NS disaccharide group content of the second intermediate NS2S; and (c) the NS2S6S, NS6S, NS2S, and NS disaccharide group content of the third intermediate NS2S6S/TriS in the synthesis of bioequivalent heparin. The first intermediate NS was of the appropriate weight average molecular weight (Mw) and molecular weight distribution to afford a second and third intermediate of the appropriate molecular weight to afford a biosynthetic heparin within the USP specifications.

SUMMARY OF BATCHES THAT MEET PORCINE USP HEPARIN SPECIFICATIONS

Batches of a, b, c and d were disclosed in U. S. provisional application on 62/384,341. The disaccharide data in the table in this section is mol %. The mol % value shown can be represented as w/w % as appeared in the U.S. provisional application on 62/384,341.

| | 0S | NS | 6S | 2S | NS6S | NS2S | 2S6S | TriS | Anti-Xa | Anti-IIa | Xa/IIa |
|---|---|---|---|---|---|---|---|---|---|---|---|
| Batch a | | | | | | | | | | | |
| NS First Intermediate | 7.9 | 92.1 | — | — | — | — | — | — | | | — |

-continued

| | 0S | NS | 6S | 2S | NS6S | NS2S | 2S6S | TriS | Anti-Xa | Anti-IIa | Xa/IIa |
|---|---|---|---|---|---|---|---|---|---|---|---|
| Second Intermediate NS2S | 7.2 | 20.3 | 0.0 | — | — | 72.5 | — | — | | | |
| Third Intermediate NS2S6S | 2.6 | 5.0 | 5.3 | 0.3 | 15.1 | 12.0 | 0.4 | 59.4 | | | |
| Product BSH batch a | 3.2 | 4.5 | 2.1 | 0.4 | 12.9 | 7.1 | 0.4 | 69.5 | 300 | 320 | 0.94 |
| Batch b | | | | | | | | | | | |
| NS First Intermediate | 7.9 | 92.1 | — | — | — | — | — | — | | | — |
| Second Intermediate NS2S | 7.2 | 20.3 | 0.0 | — | — | 72.5 | — | — | | | |
| Third Intermediate NS2S6S | 2.6 | 5.0 | 5.3 | 0.3 | 15.1 | 12.0 | 0.4 | 59.4 | | | |
| Product BSH batch b | 2.9 | 4.3 | 2.3 | 0.4 | 12.6 | 7.1 | 0.4 | 69.9 | 320 | 300 | 1.07 |
| Batch c | | | | | | | | | | | |
| NS First Intermediate | 7.9 | 92.1 | — | — | — | — | — | — | | | — |
| Second Intermediate NS2S | 7.2 | 19.9 | — | 0.9 | — | 72.1 | — | — | | | |
| Third Intermediate NS2S6S | 6.5 | 12.2 | 2.5 | 0.9 | 10.6 | 13.8 | 0.2 | 53.3 | | | |
| Product BSH batch c | 6.3 | 10.4 | 1.2 | 0.7 | 8.9 | 12.7 | 0.1 | 59.8 | 249 | 225 | 1.11 |
| Batch d | | | | | | | | | | | |
| NS First Intermediate | 7.9 | 92.1 | — | — | — | — | — | — | | | — |
| Second Intermediate NS2S | 7.2 | 19.9 | — | 0.9 | — | 72.1 | — | — | | | |
| Third Intermediate NS2S6S | 6.5 | 12.2 | 2.5 | 0.9 | 10.6 | 13.8 | 0.2 | 53.3 | | | |
| Product BSH batch d | 6.2 | 10.3 | 0.8 | 0.7 | 8.9 | 12.5 | 0.0 | 60.5 | 254 | 232 | 1.09 |
| Batch e | | | | | | | | | | | |
| NS First Intermediate | 21.7 | 78.3 | — | — | — | — | — | — | | | — |
| Second Intermediate NS2S | 19.3 | 31.9 | — | 3.8 | — | 44.9 | — | — | | | |
| Third Intermediate NS2S6S | 9.3 | 11.9 | 13.7 | 0.0 | 28.0 | 1.6 | 0.0 | 35.5 | | | |
| Product BSH batch e | 15.9 | 13.1 | 11.5 | 0.8 | 11.5 | 2.2 | 0.0 | 45.0 | 369 | 346 | 1.07 |
| Batch f | | | | | | | | | | | |
| NS First Intermediate | 21.7 | 78.3 | — | — | — | — | — | — | | | — |
| Second Intermediate NS2S | 18.4 | 30.1 | — | 2.6 | — | 48.9 | — | — | | | |
| Third Intermediate NS2S6S | 9.0 | 11.9 | 14.4 | 1.9 | 28.5 | 1.9 | 1.2 | 31.3 | | | |
| Product BSH batch f | 16.9 | 14.9 | 11.8 | 0.9 | 11.3 | 2.0 | 0.0 | 42.2 | 454 | 456 | 1.00 |
| Batch g | | | | | | | | | | | |
| NS First Intermediate | 18.1 | 81.9 | — | — | — | — | — | — | | | — |
| Second Intermediate NS2S | 15.2 | 30.8 | — | 1.6 | — | 52.4 | — | — | | | |

-continued

| | 0S | NS | 6S | 2S | NS6S | NS2S | 2S6S | TriS | Anti-Xa | Anti-IIa | Xa/IIa |
|---|---|---|---|---|---|---|---|---|---|---|---|
| Third Intermediate NS2S6S | 8.8 | 13.7 | 11.3 | 1.4 | 29.5 | 3.9 | 0.0 | 31.5 | | | |
| Product BSH batch g | 13.9 | 19.0 | 5.9 | 0.5 | 15.5 | 3.3 | 0.0 | 41.9 | 355 | 307 | 1.16 |
| Batch h | | | | | | | | | | | |
| NS First Intermediate | 14.6 | 85.4 | — | — | — | — | — | — | | — | |
| Second Intermediate NS2S | — | 1.0 | — | 60.0 | — | — | — | 1.0 | | | |
| Third Intermediate NS2S6S | 11.8 | 16.6 | 3.2 | 0.8 | 10.5 | 13.5 | 0.1 | 43.5 | | | |
| 1$^{st}$ 3OST | 12.6 | 16.1 | 1.7 | 0.7 | 9.1 | 14.8 | 0.0 | 44.9 | — | 163 | — |
| Product BSH batch h (2$^{nd}$ 3OST) | 15.1 | 17.1 | 0.7 | 0.5 | 5.7 | 12.5 | 0.0 | 48.4 | 365 | 396 | 0.92 |
| Batch i | | | | | | | | | | | |
| NS First Intermediate | 14.6 | 85.4 | — | — | — | — | — | — | | — | |
| Second Intermediate NS2S | 10.7 | 16.7 | — | 3.7 | — | 68.9 | — | — | | | |
| Third Intermediate NS2S6S | 2.0 | 1.3 | 10.5 | 0.1 | 17.1 | 0.6 | 3.2 | 65.2 | | | |
| Product BSH batch i | 1.6 | 1.5 | 4.3 | 0.3 | 6.6 | 0.9 | 1.3 | 83.6 | 712 | 855 | 0.83 |
| Batch j | | | | | | | | | | | |
| NS First Intermediate | 9.6 | 90.4 | — | — | — | — | — | — | | — | |
| Second Intermediate NS2S | 6.2 | 13.2 | — | 3.2 | — | 77.4 | — | — | | | |
| Third Intermediate NS2S6S | 3.2 | 6.1 | 4.7 | 1.2 | 10.0 | 8.3 | 0.0 | 66.5 | | | |
| Product BSH batch j | 3.5 | 5.5 | 1.2 | 0.7 | 4.3 | 5.3 | 0.0 | 79.6 | 389 | 451 | 0.86 |
| Batch k | | | | | | | | | | | |
| NS First Intermediate | 9.6 | 90.4 | — | — | — | — | — | — | | — | |
| Second Intermediate NS2S | 6.2 | 13.2 | — | 3.2 | — | 77.4 | — | — | | | |
| Third Intermediate NS2S6S | 1.7 | 1.6 | 5.6 | 0.0 | 13.2 | 2.6 | 2.6 | 72.7 | | | |
| Product BSH batch k | 1.0 | 1.8 | 2.1 | 0.4 | 5.4 | 3.6 | 0.8 | 84.9 | 503 | 599 | 0.84 |
| Batch l | | | | | | | | | | | |
| NS First Intermediate | 9.2 | 90.8 | — | — | — | — | — | — | | — | |
| Second Intermediate NS2S | 8.8 | 22.9 | — | 0.5 | — | 67.8 | — | — | | | |
| Third Intermediate NS2S6S | 6.8 | 13.2 | 2.0 | 0.5 | 11.2 | 12.5 | 0.1 | 53.7 | | | |
| Product BEqH batch l | 8.1 | 13.2 | 0.0 | 0.6 | 8.9 | 10.4 | 0.0 | 58.9 | 299 | 312 | 0.96 |
| Batch m | | | | | | | | | | | |
| NS First Intermediate | 7.9 | 92.1 | — | — | — | — | — | — | | — | |
| Second Intermediate NS2S | 6.8 | 21.4 | — | 1.9 | — | 69.8 | — | — | | | |

-continued

| | 0S | NS | 6S | 2S | NS6S | NS2S | 2S6S | TriS | Anti-Xa | Anti-IIa | Xa/IIa |
|---|---|---|---|---|---|---|---|---|---|---|---|
| Third Intermediate NS2S6S | 5.0 | 9.4 | 3.0 | 0.6 | 11.5 | 12.0 | 0.2 | 58.3 | | | |
| 1st 3OST | | | | | — | | | | — | 160 | — |
| Product BSH batch m (2nd 3OST) | 6.3 | 9.3 | 1.2 | 0.4 | 10.4 | 10.4 | 0.0 | 62.1 | 209 | 203 | 1.03 |
| Batch n | | | | | | | | | | | |
| NS First Intermediate | 7.9 | 92.1 | — | — | — | — | — | — | | — | |
| Second Intermediate NS2S | 7.2 | 19.9 | — | 0.9 | — | 72.1 | — | — | | | |
| Third Intermediate NS2S6S | 6.5 | 12.2 | 2.5 | 0.9 | 10.6 | 13.8 | 0.2 | 53.3 | | | |
| Product BSH batch n | 6.5 | 11.2 | 0.6 | 0.9 | 8.8 | 13.5 | 0.0 | 58.5 | 220 | 244 | 0.90 |
| Batch o | | | | | | | | | | | |
| NS First Intermediate | 7.3 | 92.7 | — | — | — | — | — | — | | — | |
| Second Intermediate NS2S | 7.6 | 38.6 | — | 0.1 | — | 53.6 | — | — | | | |
| Third Intermediate NS2S6S | 4.3 | 11.4 | 4.8 | 0.0 | 39.4 | 2.1 | 0.0 | 38.1 | | | |
| Product BSH batch o | 6.8 | 13.3 | 1.4 | 0.0 | 21.8 | 1.3 | 0.0 | 55.5 | 441 | 578 | 0.76 |
| Batch p | | | | | | | | | | | |
| NS First Intermediate | 7.3 | 92.7 | — | — | — | — | — | — | | — | |
| Second Intermediate NS2S | 6.9 | 30.1 | — | 0.3 | — | 62.7 | — | — | | | |
| Third Intermediate NS2S6S | 6.5 | 18.3 | 2.5 | 0.0 | 20.8 | 7.2 | 0.0 | 44.7 | | | |
| Product BSH batch p | 8.9 | 19.2 | 0.3 | 0.0 | 12.1 | 6.5 | 0.0 | 53.0 | 407 | 448 | 0.91 |
| Batch q | | | | | | | | | | | |
| NS First Intermediate | 7.3 | 92.7 | — | — | — | — | — | — | | — | |
| Second Intermediate NS2S | 6.5 | 24.0 | — | 0.6 | — | 68.9 | — | — | | | |
| Third Intermediate NS2S6S | 2.3 | 4.5 | 4.3 | 0.4 | 19.9 | 24.8 | 0.3 | 43.5 | | | |
| Product BSH batch q | 2.6 | 4.8 | 2.3 | 0.4 | 14.9 | 27.1 | 0.2 | 47.7 | 288 | 262 | 1.10 |
| Batch r | | | | | | | | | | | |
| NS First Intermediate | 7.3 | 92.7 | — | — | — | — | — | — | | — | |
| Second Intermediate NS2S | 6.5 | 24.0 | — | 0.6 | — | 68.9 | — | — | | | |
| Third Intermediate NS2S6S | 1.8 | 3.3 | 4.9 | 0.3 | 21.3 | 20.1 | 0.3 | 47.9 | | | |
| 1st 3OST | 1.9 | 3.8 | 2.5 | 0.3 | 15.5 | 23.1 | 0.2 | 52.6 | 362 | 301 | 1.20 |
| Product BSH batch r (2nd 3OST) | 2.3 | 4.4 | 1.5 | 0.2 | 12.5 | 21.6 | 0.0 | 57.5 | 438 | 438 | 1.00 |
| Batch s | | | | | | | | | | | |
| NS First Intermediate | 7.3 | 92.7 | — | — | — | — | — | — | | — | |
| Second Intermediate NS2S | 6.8 | 21.5 | — | 0.7 | — | 71.0 | — | — | | | |

-continued

| | 0S | NS | 6S | 2S | NS6S | NS2S | 2S6S | TriS | Anti-Xa | Anti-IIa | Xa/IIa |
|---|---|---|---|---|---|---|---|---|---|---|---|
| Third Intermediate NS2S6S | 4.8 | 11.7 | 2.4 | 1.0 | 10.2 | 16.8 | 0.0 | 53.0 | | | |
| Product BSH batch s | 3.9 | 6.5 | 1.1 | 1.1 | 10.0 | 12.3 | 0.5 | 64.7 | 280 | 301 | 0.93 |
| Batch t | | | | | | | | | | | |
| NS First Intermediate | 7.3 | 92.7 | — | — | — | — | — | — | | — | |
| Second Intermediate NS2S | 6.5 | 20.4 | — | 0.7 | — | 72.4 | — | — | | | |
| Third Intermediate NS2S6S | 5.6 | 13.9 | 1.1 | 0.9 | 6.1 | 20.0 | 0.0 | 52.3 | | | |
| 1$^{st}$ 3OST | | | | | — | | | | 132 | 148 | 0.89 |
| Product BSH batch t (2$^{nd}$ 3OST) | 5.8 | 12.2 | 0.3 | 1.1 | 5.7 | 15.1 | 0.0 | 59.7 | 220 | 231 | 0.95 |
| Batch u | | | | | | | | | | | |
| NS First Intermediate | 7.3 | 92.7 | — | — | — | — | — | — | | — | |
| Second Intermediate NS2S | 6.5 | 20.4 | — | 0.7 | — | 72.4 | — | — | | | |
| Third Intermediate NS2S6S | 4.7 | 11.2 | 1.2 | 0.9 | 8.4 | 14.2 | 0.0 | 59.3 | | | |
| Product BSH batch u | 5.4 | 10.9 | 0.4 | 1.1 | 6.8 | 14.1 | 0.1 | 61.3 | 207 | 220 | 0.94 |
| Batch v | | | | | | | | | | | |
| NS First Intermediate | 7.3 | 92.7 | — | — | — | — | — | — | | — | |
| Second Intermediate NS2S | 6.8 | 16.8 | — | 1.0 | — | 75.4 | — | — | | | |
| Third Intermediate NS2S6S | 2.0 | 3.4 | 4.5 | 0.5 | 13.4 | 26.6 | 0.5 | 49.2 | | | |
| Product BSH batch v | 2.0 | 3.4 | 1.9 | 0.5 | 9.3 | 28.0 | 0.3 | 54.6 | 331 | 303 | 1.09 |
| Batch w | | | | | | | | | | | |
| NS First Intermediate | 7.3 | 92.7 | — | — | — | — | — | — | | — | |
| Second Intermediate NS2S | 6.8 | 16.8 | — | 1.0 | — | 75.4 | — | — | | | |
| Third Intermediate NS2S6S | 1.5 | 2.5 | 4.9 | 0.4 | 14.3 | 21.4 | 0.6 | 54.5 | | | |
| Product BSH batch w | 1.5 | 2.7 | 1.8 | 0.4 | 9.3 | 23.5 | 0.3 | 60.5 | 393 | 343 | 1.145 |
| Batch x | | | | | | | | | | | |
| NS First Intermediate | 7.3 | 92.7 | — | — | — | — | — | — | | — | |
| Second Intermediate NS2S | 6.8 | 16.8 | — | 1.0 | — | 75.4 | — | — | | | |
| Third Intermediate NS2S6S | 1.0 | 1.4 | 5.5 | 0.3 | 15.4 | 12.1 | 0.7 | 63.7 | | | |
| 1$^{st}$ 3OST | 0.6 | 1.5 | 2.4 | 0.3 | 10.2 | 13.6 | 0.5 | 70.9 | 417 | 331 | 1.26 |
| Product BSH batch x (2$^{nd}$ 3OST) | 0.9 | 1.6 | 1.5 | 0.2 | 8.3 | 12.7 | 0.1 | 74.7 | 472 | 463 | 1.02 |
| Batch y | | | | | | | | | | | |
| NS First Intermediate | 7.3 | 92.7 | — | — | — | — | — | — | | — | |
| Second Intermediate NS2S | 5.8 | 13.4 | — | 1.4 | — | 79.4 | — | — | | | |

-continued

|  | 0S | NS | 6S | 2S | NS6S | NS2S | 2S6S | TriS | Anti-Xa | Anti-IIa | Xa/IIa |
|---|---|---|---|---|---|---|---|---|---|---|---|
| Third Intermediate NS2S6S | 1.4 | 3.5 | 5.5 | 0.0 | 15.1 | 4.9 | 0.0 | 69.6 | | | |
| Product BSH batch y | 1.2 | 3.5 | 1.4 | 0.0 | 4.0 | 0.9 | 0.0 | 89.0 | 385 | 486 | 0.79 |
| Batch z | | | | | | | | | | | |
| NS First Intermediate | 0.7 | 99.3 | — | — | — | — | — | — | | — | |
| Second Intermediate NS2S | 0.5 | 30.5 | — | 0.0 | — | 69.0 | — | — | | | |
| Third Intermediate NS2S6S | 0.4 | 21.1 | 0.4 | 0.0 | 22.8 | 7.5 | 0.0 | 47.9 | | | |
| Product BSH batch z | 0.5 | 21.7 | 0.5 | 0.0 | 12.6 | 6.7 | 0.0 | 58.0 | 227 | 251 | 0.90 |

Summary Information:

TABLE 7

Summary of NS % in first intermediate NS

| NSH | NS |
|---|---|
| Batch a | 92.1 |
| Batch b | 92.1 |
| Batch c | 92.1 |
| Batch d | 92.1 |
| Batch e | 78.3 |
| Batch f | 78.3 |
| Batch g | 81.9 |
| Batch h | 85.4 |
| Batch i | 85.4 |
| Batch j | 90.4 |
| Batch k | 90.4 |
| Batch l | 90.8 |
| Batch m | 92.1 |
| Batch n | 92.1 |
| Batch o | 92.7 |
| Batch p | 92.7 |
| Batch q | 92.7 |
| Batch r | 92.7 |
| Batch s | 92.7 |
| Batch t | 92.7 |
| Batch u | 92.7 |
| Batch v | 92.7 |
| Batch w | 92.7 |
| Batch x | 92.7 |
| Batch y | 92.7 |
| Batch z | 99.3 |
| Min | 78.3 |
| Max | 99.3 |
| Range | 78.3-99.3 |

TABLE 8

Summary of NS, NS2S % in second intermediate NS2S

| NS2S | 0S | NS | 2S | NS2S | 0S + 2S |
|---|---|---|---|---|---|
| Batch a | 7.2 | 20.3 | 0.0 | 72.5 | 7.2 |
| Batch b | 7.2 | 20.3 | 0.0 | 72.5 | 7.2 |
| Batch c | 7.2 | 19.9 | 0.9 | 72.1 | 8.1 |
| Batch d | 7.2 | 19.9 | 0.9 | 72.1 | 8.1 |
| Batch e | 19.3 | 31.9 | 3.8 | 44.9 | 23.1 |
| Batch f | 18.4 | 30.1 | 2.6 | 48.9 | 21.0 |
| Batch g | 15.2 | 30.8 | 1.6 | 52.4 | 16.8 |
| Batch h | 13.8 | 25.2 | 1.0 | 60.0 | 14.8 |
| Batch i | 10.7 | 16.7 | 3.7 | 68.9 | 14.5 |
| Batch j | 6.2 | 13.2 | 3.2 | 77.4 | 9.4 |
| Batch k | 6.2 | 13.2 | 3.2 | 77.4 | 9.4 |
| Batch l | 8.8 | 22.9 | 0.5 | 67.8 | 9.3 |
| Batch m | 6.8 | 21.4 | 1.9 | 69.8 | 8.7 |
| Batch n | 7.2 | 19.9 | 0.9 | 72.1 | 8.1 |
| Batch o | 7.6 | 38.6 | 0.1 | 53.6 | 7.7 |
| Batch p | 6.9 | 30.1 | 0.3 | 62.7 | 7.2 |
| Batch q | 6.5 | 24.0 | 0.6 | 68.9 | 7.1 |
| Batch r | 6.5 | 24.0 | 0.6 | 68.9 | 7.1 |
| Batch s | 6.8 | 21.5 | 0.7 | 71.0 | 7.5 |
| Batch t | 6.5 | 20.4 | 0.7 | 72.4 | 7.2 |
| Batch u | 6.5 | 20.4 | 0.7 | 72.4 | 7.2 |
| Batch v | 6.8 | 16.8 | 1.0 | 75.4 | 7.8 |
| Batch w | 6.8 | 16.8 | 1.0 | 75.4 | 7.8 |
| Batch x | 6.8 | 16.8 | 1.0 | 75.4 | 7.8 |
| Batch y | 5.8 | 13.4 | 1.4 | 79.4 | 7.2 |
| Batch z | 0.5 | 30.5 | 0.0 | 69.0 | 0.5 |
| Min | 0.5 | 13.2 | 0.0 | 44.9 | 0.5 |
| Max | 19.3 | 38.6 | 3.8 | 79.4 | 23.1 |
| Range | 0.5-19.3 | 13.2-38.6 | 0.0-3.8 | 44.9-79.4 | 0.5-23.1 |

TABLE 9

Summary of NS, NS2S, NS6S, TriS % in third intermediate NS2S6S

| TriS (NS2S6S) | 0S | NS | 6S | 2S | NS6S | NS2S | 2S6S | TriS | 0S + 6S + 2S + 2S6S |
|---|---|---|---|---|---|---|---|---|---|
| Batch a | 2.6 | 5.0 | 5.3 | 0.3 | 15.1 | 12.0 | 0.4 | 59.4 | 8.6 |
| Batch b | 2.6 | 5.0 | 5.3 | 0.3 | 15.1 | 12.0 | 0.4 | 59.4 | 8.6 |
| Batch c | 6.5 | 12.2 | 2.5 | 0.9 | 10.6 | 13.8 | 0.2 | 53.3 | 10.1 |
| Batch d | 6.5 | 12.2 | 2.5 | 0.9 | 10.6 | 13.8 | 0.2 | 53.3 | 10.1 |
| Batch e | 9.3 | 11.9 | 13.7 | 0.0 | 28.0 | 1.6 | 0.0 | 35.5 | 23.0 |
| Batch f | 9.0 | 11.9 | 14.4 | 1.9 | 28.5 | 1.9 | 1.2 | 31.3 | 26.5 |
| Batch g | 8.8 | 13.7 | 11.3 | 1.4 | 29.5 | 3.9 | 0.0 | 31.5 | 21.4 |
| Batch h | 11.8 | 16.6 | 3.2 | 0.8 | 10.5 | 13.5 | 0.1 | 43.5 | 15.9 |

TABLE 9-continued

Summary of NS, NS2S, NS6S, TriS % in third intermediate NS2S6S

| TriS (NS2S6S) | 0S | NS | 6S | 2S | NS6S | NS2S | 2S6S | TriS | 0S + 6S + 2S + 2S6S |
|---|---|---|---|---|---|---|---|---|---|
| Batch i | 2.0 | 1.3 | 10.5 | 0.1 | 17.1 | 0.6 | 3.2 | 65.2 | 15.8 |
| Batch j | 3.2 | 6.1 | 4.7 | 1.2 | 10.0 | 8.3 | 0.0 | 66.5 | 9.1 |
| Batch k | 1.7 | 1.6 | 5.6 | 0.0 | 13.2 | 2.6 | 2.6 | 72.7 | 9.9 |
| Batch l | 6.8 | 13.2 | 2.0 | 0.5 | 11.2 | 12.5 | 0.1 | 53.7 | 9.4 |
| Batch m | 5.0 | 9.4 | 3.0 | 0.6 | 11.5 | 12.0 | 0.2 | 58.3 | 8.8 |
| Batch n | 6.5 | 12.2 | 2.5 | 0.9 | 10.6 | 13.8 | 0.2 | 53.3 | 10.1 |
| Batch o | 4.3 | 11.4 | 4.8 | 0.0 | 39.4 | 2.1 | 0.0 | 38.1 | 9.1 |
| Batch p | 6.5 | 18.3 | 2.5 | 0.0 | 20.8 | 7.2 | 0.0 | 44.7 | 9.0 |
| Batch q | 2.3 | 4.5 | 4.3 | 0.4 | 19.9 | 24.8 | 0.3 | 43.5 | 7.3 |
| Batch r | 1.8 | 3.3 | 4.9 | 0.3 | 21.3 | 20.1 | 0.3 | 47.9 | 7.3 |
| Batch s | 4.8 | 11.7 | 2.4 | 1.0 | 10.2 | 16.8 | 0.0 | 53.0 | 8.2 |
| Batch t | 5.6 | 13.9 | 1.1 | 0.9 | 6.1 | 20.0 | 0.0 | 52.3 | 7.6 |
| Batch u | 4.7 | 11.2 | 1.2 | 0.9 | 8.4 | 14.2 | 0.0 | 59.3 | 6.8 |
| Batch v | 2.0 | 3.4 | 4.5 | 0.5 | 13.4 | 26.6 | 0.5 | 49.2 | 7.5 |
| Batch w | 1.5 | 2.5 | 4.9 | 0.4 | 14.3 | 21.4 | 0.6 | 54.5 | 7.4 |
| Batch x | 1.0 | 1.4 | 5.5 | 0.3 | 15.4 | 12.1 | 0.7 | 63.7 | 7.5 |
| Batch y | 1.4 | 3.5 | 5.5 | 0.0 | 15.1 | 4.9 | 0.0 | 69.6 | 6.9 |
| Batch z | 0.4 | 21.1 | 0.4 | 0.0 | 22.8 | 7.5 | 0.0 | 47.9 | 0.8 |
| Min | 0.4 | 1.3 | 0.4 | 0.0 | 6.1 | 0.6 | 0.0 | 31.3 | 0.8 |
| Max | 11.8 | 21.1 | 14.4 | 1.9 | 39.4 | 26.6 | 3.2 | 72.7 | 26.5 |
| Range | 0.4-11.8 | 1.3-21.1 | 0.4-14.4 | 0.0-1.9 | 6.1-39.4 | 0.6-26.6 | 0.0-3.2 | 31.3-72.7 | 0.8-26.5 |

TABLE 10

Summary of reaction scales and volumes for biosynthetic heparins

| BEqH | Scale (mg or mL) |
|---|---|
| Batch a | 3 |
| Batch b | 3 |
| Batch c | 3 |
| Batch d | 3 |
| Batch e | 3 |
| Batch f | 3 |
| Batch g | 3 |
| Batch h | 3 |
| Batch i | 3 |
| Batch j | 3 |
| Batch k | 3 |
| Batch l | 1000 |
| Batch m | 100 |
| Batch n | 100 |
| Batch o | 3 |
| Batch p | 3 |
| Batch q | 3 |
| Batch r | 3 |
| Batch s | 100 |
| Batch t | 3 |
| Batch u | 3 |
| Batch v | 3 |
| Batch w | 3 |
| Batch x | 3 |
| Batch y | 3 |
| Batch z | 3 |

In sum, it may be important to use the first intermediate NS with specific NS group content, Mw, and molecular weight distribution shown the above to successfully obtain specific second and third intermediates, and finally to afford B SH that may meet USP heparin criteria.

TABLE 11

Disaccharide data in w/w % of BSH batches a, b, c and d. These batches were disclosed in U.S. provisional application on 62/384,341 and are also BEqH.

| | 0S | NS | 6S | 2S | NS6S | NS2S | 2S6S | TriS | Anti-Xa | Anti-IIa | Xa/IIa |
|---|---|---|---|---|---|---|---|---|---|---|---|
| | | | | w/w % | | | | | | | |
| Batch a | | | | | | | | | | | |
| NS First Intermediate | 6.2 | 93.8 | 0.0 | 0.0 | 0.0 | 0.0 | 0.0 | 0.0 | | — | |
| Second Intermediate NS2S | 6.0 | 20.2 | 0.0 | 0.0 | 0.0 | 73.8 | 0.0 | 0.0 | | | |
| Third Intermediate NS2S6S | 1.5 | 3.1 | 2.0 | 0.3 | 22.2 | 8.4 | 0.5 | 62.0 | | | |
| Product BSH batch a | 1.7 | 2.6 | 0.8 | 0.2 | 18.6 | 5.1 | 0.4 | 70.6 | 300 | 320 | 0.94 |
| Batch b | | | | | | | | | | | |
| NS First Intermediate | 6.2 | 93.8 | 0.0 | 0.0 | 0.0 | 0.0 | 0.0 | 0.0 | | — | |

TABLE 11-continued

Disaccharide data in w/w % of BSH batches a, b, c and d. These batches were disclosed in U.S. provisional application on 62/384,341 and are also BEqH.

| | 0S | NS | 6S | 2S | NS6S w/w % | NS2S | 2S6S | TriS | Anti-Xa | Anti-IIa | Xa/IIa |
|---|---|---|---|---|---|---|---|---|---|---|---|
| Second Intermediate NS2S | 6.0 | 20.2 | 0.0 | 0.0 | 0.0 | 73.8 | 0.0 | 0.0 | | | |
| Third Intermediate NS2S6S | 1.5 | 3.1 | 2.0 | 0.3 | 22.2 | 8.4 | 0.5 | 62.0 | | | |
| Product BSH batch b | 1.5 | 2.6 | 0.9 | 0.2 | 18.2 | 5.1 | 0.5 | 71.1 | 320 | 300 | 1.07 |
| Batch c | | | | | | | | | | | |
| NS First Intermediate | 6.2 | 93.8 | 0.0 | 0.0 | 0.0 | 0.0 | 0.0 | 0.0 | — | | |
| Second Intermediate NS2S | 5.6 | 18.5 | 0.0 | 0.9 | 0.0 | 75.3 | 0.0 | 0.0 | | | |
| Third Intermediate NS2S6S | 3.8 | 8.1 | 1.0 | 0.6 | 17.7 | 10.9 | 0.6 | 57.4 | | | |
| Product BSH batch c | 3.5 | 5.9 | 0.4 | 0.4 | 14.5 | 9.4 | 0.1 | 65.6 | 249 | 225 | 1.11 |
| Batch d | | | | | | | | | | | |
| NS First Intermediate | 6.2 | 93.8 | 0.0 | 0.0 | 0.0 | 0.0 | 0.0 | 0.0 | — | | |
| Second Intermediate NS2S | 5.6 | 18.5 | 0.0 | 0.9 | 0.0 | 75.3 | 0.0 | 0.0 | | | |
| Third Intermediate NS2S6S | 3.8 | 8.1 | 1.0 | 0.6 | 17.7 | 10.9 | 0.6 | 57.4 | | | |
| Product BSH batch d | 3.5 | 5.9 | 0.3 | 0.4 | 14.5 | 9.3 | 0.1 | 66.1 | 254 | 232 | 1.09 |

The person of ordinary skill would understand that disaccharide data can be expressed in either mol % (as used herein) or weight % (as used in the provisional application).

Biosynthetic heparin batches that appeared in the U.S. provisional application on 62/384,341 and that do not meet porcine USP Heparin activity and molecular weight specifications The provisional application included two batches that do not meet porcine USP Heparin activity and molecular weight specifications. Tables 12 and 13 below summarize the data. Disaccharide values are expressed both in w/w % and mol %.

TABLE 12

| | NS | NS6S (w/w %) | NS2S | TriS | NS | NS6S (mol %) | NS2S | TriS | Anti-Xa (U/mg) | Anti-IIa (U/mg) | Xa/IIa |
|---|---|---|---|---|---|---|---|---|---|---|---|
| Non-equivalent batch 1 | | | | | | | | | | | |
| NS First Intermediate # | No Data | — | — | — | 81.9 | — | — | — | — | — | — |
| Second Intermediate NS2S * | 16.3 | — | 77.4 | — | No Data | No Data | No Data | No Data | — | — | — |
| Third Intermediate NS2S6S * | 22.7 | 4.4 | 16.7 | 52.5 | No Data | No Data | No Data | No Data | — | — | — |
| Non-equivalent BEH batch 1 * | 10.6 | 5.1 | 7.4 | 73.3 | No Data | No Data | No Data | No Data | 97 | 133 | 1.4 |
| Non-equivalent batch 2 | | | | | | | | | | | |
| NS First Intermediate # | No Data | — | — | — | 95.1 | — | — | — | — | — | — |
| Second Intermediate NS2S | 11.0 | — | 84.6 | — | 10.0 | — | 84.3 | — | — | — | — |

TABLE 12-continued

| | NS | NS6S | NS2S | TriS | NS | NS6S | NS2S | TriS | Anti-Xa (U/mg) | Anti-IIa (U/mg) | Xa/IIa |
|---|---|---|---|---|---|---|---|---|---|---|---|
| | | (w/w %) | | | | (mol %) | | | | | |
| Third Intermediate NS2S6S | 6.2 | 5.3 | 19.0 | 64.8 | 7.2 | 3.1 | 22.6 | 60.8 | — | — | — |
| Nonequivalent BEH batch 2 | 5.4 | 5.5 | 15.9 | 68.8 | 6.5 | 3.4 | 19.2 | 65.4 | 130 | 130 | 1.0 |

\# measured by $^1$H-NMR,
\* measured by LC-MS

TABLE 13

Summary of molecular weights

| | | $M_W$ | $M_{24000}$ | $M_{8000-16000}/M_{16000-24000}$ |
|---|---|---|---|---|
| | | USP specification | | |
| | | 15,000-19,000 | Not more than 20% | Not less than 1.0 |
| Nonequivalent Batch 1 | Starting Intermediate 1 | 21,400 | 31.5 | 0.6 |
| | BSH Batch 1 | 30,300 | 59.0 | 0.6 |
| Nonequivalent Batch 2 | Starting Intermediate 1 | 18,400 | 22.0 | 1.3 |
| | BSH Batch 2 | 19,000 | 22.3 | 1.2 |

Although the foregoing refers to particular preferred embodiments, it will be understood that the present invention is not so limited. It will occur to those of ordinary skill in the art that various modifications may be made to the disclosed embodiments and that such modifications are intended to be within the scope of the present invention.

All of the publications, patent applications and patents cited in this specification are incorporated herein by reference in their entirety.

What is claimed is:

1. A glycosaminoglycan comprising (a) 44-80% of N-sulfated, 2-sulfated (NS2S) disaccharide group; (b) 13-39% of NS disaccharide group and (c) 0.4-25% of at least one unmodified N-acetylated glucosamine group selected from OS disaccharide group and 2S disaccharide group, wherein the glycosaminoglycan has a weight average molecular weight appropriate to form a final heparin product of 15,000-19,000 Da, the percentage of heparin chains with a molecular weight of greater than 24,000 Da being not more than 20% of the total, and the ratio of chains between molecular weights of 8,000 to 16,000 Da to the percentage of chains with molecular weights of 16,000 to 24,000 Da being not less than 1.0.

2. The glycosaminoglycan of claim 1, wherein an amount of the NS2S disaccharide group in the glycosaminoglycan is 50-78%.

3. The glycosaminoglycan of claim 1, wherein an amount of the NS2S disaccharide group in the glycosaminoglycan is 55-77%.

4. The glycosaminoglycan of claim 1, wherein an amount of the NS2S disaccharide group in the glycosaminoglycan is 60-76%.

5. The glycosaminoglycan of claim 1, wherein an amount of the NS disaccharide group in the glycosaminoglycan is 14-35%.

6. The glycosaminoglycan of claim 1, wherein an amount of the NS disaccharide group in the glycosaminoglycan is 15-30%.

7. The glycosaminoglycan of claim 1, wherein an amount of the NS disaccharide group in the glycosaminoglycan is 16-26%.

8. A method of making a second glycosaminoglycan intermediate, which is the glycosaminoglycan of claim 7; the method comprising:
  a. converting an amount of N-acetyl glucosamine residues in heparosan to produce a first glycosaminoglycan comprising 78-99% of N-sulfated (NS) disaccharide group, wherein the amount of the converted N-acetyl glucosamine residues corresponds to the amount of the NS group in the first glycosaminoglycan intermediate; and
  b. treating the first glycosaminoglycan intermediate with an enzyme, which is C5-epimerase (C5-epi) and 2-O-sulfotransferase (2OST), in the presence of a sulfate donor to produce the second glycosaminoglycan intermediate.

9. The method of claim 8, wherein said converting comprises reacting the heparosan with a base and a sulfonating reagent.

10. The method of claim 8, wherein said converting comprises reacting the heparosan with N-deacetylase, N-sulfotransferase (NDST).

11. A method of making a third glycosaminoglycan intermediate comprising 31-73% of NS2S6S disaccharide group, 6-40% of NS6S disaccharide group, 0-27% of NS2S group and 1-22% of NS group:
  the method comprising
  treating a second glycosaminoglycan intermediate, which is the glycosaminoglycan of claim 7, with an enzyme, which is 6-O-sulfotransferase isoforms 1 and/or 3 (6OST-1/3), in the presence of a sulfate donor to convert the second glycosaminoglycan intermediate to the third glycosaminoglycan intermediate.

12. The method of claim 11, wherein the sulfate donor comprises PAPS.

13. The method of claim 12, wherein PAPS is in a solution.

14. The method of claim 11, wherein the sulfate donor comprises PAP and PNPS.

15. The method of claim 11, wherein said treatment is performed in the presence of a recycling system comprising PAPS, PNPS and a catalyst.

16. The method of claim 15, wherein the catalyst is aryl sulfotransferase IV (AST-IV).

17. The method of claim 16, wherein the enzyme is in solution.

18. The method of claim 16, wherein the enzyme is immobilized.

* * * * *

UNITED STATES PATENT AND TRADEMARK OFFICE
CERTIFICATE OF CORRECTION

| | | |
|---|---|---|
| PATENT NO. | : 11,591,628 B2 | Page 1 of 1 |
| APPLICATION NO. | : 16/331127 | |
| DATED | : February 28, 2023 | |
| INVENTOR(S) | : Marc Douaisi et al. | |

It is certified that error appears in the above-identified patent and that said Letters Patent is hereby corrected as shown below:

In the Claims

Column 56, Claim 8, Line 22, "claim 7" should be --claim 1--.

Column 56, Claim 11, Line 49, "claim 7" should be --claim 1--.

Signed and Sealed this
Twenty-third Day of January, 2024

Katherine Kelly Vidal
*Director of the United States Patent and Trademark Office*